US008106008B2

(12) United States Patent
Lynch et al.

(10) Patent No.: US 8,106,008 B2
(45) Date of Patent: Jan. 31, 2012

(54) COMPOSITIONS AND METHODS FOR ARTHRODETIC PROCEDURES

(75) Inventors: Samuel E. Lynch, Franklin, TN (US); Charles E. Hart, Brentwood, TN (US)

(73) Assignee: BioMimetic Therapeutics, Inc., Franklin, TN (US)

( * ) Notice: Subject to any disclaimer, the term of this patent is extended or adjusted under 35 U.S.C. 154(b) by 0 days.

(21) Appl. No.: 12/513,491

(22) PCT Filed: Nov. 5, 2007

(86) PCT No.: PCT/US2007/083638
§ 371 (c)(1),
(2), (4) Date: Feb. 23, 2010

(87) PCT Pub. No.: WO2008/073628
PCT Pub. Date: Jun. 19, 2008

(65) Prior Publication Data
US 2010/0136085 A1 Jun. 3, 2010

Related U.S. Application Data

(60) Provisional application No. 60/856,588, filed on Nov. 3, 2006.

(51) Int. Cl.
A61K 38/18 (2006.01)
A61F 2/00 (2006.01)
A61F 13/00 (2006.01)
(52) U.S. Cl. .......... 514/8.2; 424/422; 424/423; 424/426
(58) Field of Classification Search .................. None
See application file for complete search history.

(56) References Cited

U.S. PATENT DOCUMENTS

| | | | |
|---|---|---|---|
| 3,943,072 A | 3/1976 | Thomson et al. | |
| 4,845,075 A | 7/1989 | Murray et al. | |
| 4,861,757 A | 8/1989 | Antoniades et al. | |
| 4,874,746 A | 10/1989 | Antoniades et al. | |
| RE33,161 E | 2/1990 | Brown et al. | |
| 4,904,259 A | 2/1990 | Itay | |
| 4,963,145 A | 10/1990 | Takagi et al. | |
| 4,975,526 A | 12/1990 | Kuberasampath et al. | |
| 5,011,910 A | 4/1991 | Marshall et al. | |
| 5,013,649 A | 5/1991 | Wang et al. | |
| 5,019,559 A | 5/1991 | Antoniades et al. | |
| 5,034,375 A | 7/1991 | Antoniades et al. | |
| 5,035,887 A | 7/1991 | Antoniades et al. | |
| 5,045,633 A | 9/1991 | Murray et al. | |
| 5,053,212 A | 10/1991 | Constantz et al. | |
| 5,106,748 A | 4/1992 | Wozney et al. | |
| 5,108,922 A | 4/1992 | Wang et al. | |
| 5,112,354 A | 5/1992 | Sires | |
| 5,116,738 A | 5/1992 | Wang et al. | |
| 5,124,316 A | 6/1992 | Antoniades et al. | |
| 5,128,321 A | 7/1992 | Murray et al. | |
| 5,129,905 A | 7/1992 | Constantz | |
| 5,141,905 A | 8/1992 | Rosen et al. | |
| 5,149,691 A * | 9/1992 | Rutherford .................... 514/12 |
| 5,165,938 A | 11/1992 | Knighton | |
| 5,187,076 A | 2/1993 | Wozney et al. | |
| 5,187,263 A | 2/1993 | Murray et al. | |
| 5,219,576 A | 6/1993 | Chu et al. | |
| 5,219,759 A | 6/1993 | Heldin et al. | |
| 5,270,300 A | 12/1993 | Hunziker | |
| 5,290,708 A | 3/1994 | Ashihara et al. | |
| 5,376,636 A | 12/1994 | Rutherford et al. | |
| 5,457,093 A | 10/1995 | Cini et al. | |
| 5,460,962 A | 10/1995 | Kemp | |
| 5,516,896 A | 5/1996 | Murray et al. | |
| 5,518,680 A | 5/1996 | Cima et al. | |
| 5,531,794 A | 7/1996 | Takagi et al. | |
| 5,533,836 A | 7/1996 | Moore | |
| 5,549,123 A | 8/1996 | Okuyama et al. | |
| 5,599,558 A | 2/1997 | Gordinier et al. | |
| 5,629,191 A | 5/1997 | Cahn | |
| 5,635,372 A | 6/1997 | Celeste et al. | |
| 5,650,176 A | 7/1997 | Lee et al. | |
| 5,747,273 A | 5/1998 | Khosravi et al. | |
| 5,759,815 A | 6/1998 | Charette et al. | |
| 5,783,217 A | 7/1998 | Lee et al. | |
| 5,804,176 A | 9/1998 | Grotendorst | |

(Continued)

FOREIGN PATENT DOCUMENTS

EP 0 289 584 B1 11/1988

(Continued)

OTHER PUBLICATIONS

Aastrom Biosciences, Inc. (Mar. 23, 2006). "Aastrom Biosciences Received Orphan Drug Designation From the FDA for Proprietary Marrow Cells," located at <http://www.aastrom.com/pressreleases.asp?GetLink=http%3A%2F%2Fwww%2E7ware%...>, last visited on Feb. 24, 2010, 2 pages.

Adalberto et al. "Periodontal Regeneration," *J. Periodontal*, 2005, 76(9):1601-1622.

Adornato, M.C. et al. (Jul. 2007). "The Treatment of Bisphosphonate-Associated Osteonecrosis of the Jaws with Bone Resection and Autologous Platelet-Derived Growth Factors," *Journal of the American Dental Association* 138(7) :971-977.

Aghaloo, T.L. DDS MD et al. "Evaluation of Platelet-Rich Plasma in Combination with Anorganic Bovine Bone in the Rabbit Cranium: A Pilot Study," *The International Journal of Oral and Maxillofacial Implants*; 2004, 19:59-65.

Ahn, S-H. et al. (Jun. 2003). "Effect of Recombinant Human Bone Morphogenetic Protein-4 with Carriers in Rat Calvarial Defects," *Journal of Periodontology* 74(6):787-797.

(Continued)

*Primary Examiner* — Marianne P Allen
(74) *Attorney, Agent, or Firm* — Earl M. Douglas; Michael D. Ruse, Jr.

(57) ABSTRACT

The present invention provides compositions and methods for facilitating fusion of bones in a joint. The present invention provides compositions and methods for promoting fusion of bones in arthrodetic procedures. In one embodiment, a method of performing an arthrodetic procedure comprises providing a composition comprising PDGF disposed in a biocompatible matrix and applying the composition to a site of desired bone fusion in a joint.

50 Claims, No Drawings

U.S. PATENT DOCUMENTS

| | | |
|---|---|---|
| 5,837,258 A | 11/1998 | Grotendorst |
| 5,853,746 A | 12/1998 | Hunziker |
| 5,866,165 A | 2/1999 | Liu et al. |
| 5,962,028 A | 10/1999 | Constantz |
| 5,965,403 A | 10/1999 | Celeste et al. |
| 5,972,385 A | 10/1999 | Liu et al. |
| 6,018,095 A | 1/2000 | Lerch et al. |
| 6,027,742 A | 2/2000 | Lee et al. |
| 6,030,636 A | 2/2000 | Randolph et al. |
| 6,077,989 A | 6/2000 | Kandel et al. |
| 6,083,910 A | 7/2000 | Kunitani et al. |
| 6,136,029 A | 10/2000 | Johnson et al. |
| 6,180,606 B1 | 1/2001 | Chen et al. |
| 6,214,368 B1 | 4/2001 | Lee et al. |
| 6,221,625 B1 | 4/2001 | Ashihara et al. |
| 6,224,635 B1 | 5/2001 | Ricci et al. |
| 6,280,191 B1 | 8/2001 | Gordon |
| 6,280,478 B1 | 8/2001 | Richter et al. |
| 6,281,195 B1 | 8/2001 | Rueger et al. |
| 6,287,341 B1 | 9/2001 | Lee et al. |
| 6,313,189 B1 | 11/2001 | Wenz et al. |
| 6,316,091 B1 | 11/2001 | Richart et al. |
| 6,331,312 B1 | 12/2001 | Lee et al. |
| 6,346,123 B1 | 2/2002 | McKay |
| 6,398,972 B1 | 6/2002 | Blasetti et al. |
| 6,440,444 B2 | 8/2002 | Boyce et al. |
| 6,451,059 B1 | 9/2002 | Janas et al. |
| 6,465,205 B2 | 10/2002 | Hicks, Jr. |
| 6,468,543 B1 | 10/2002 | Gilbertson et al. |
| 6,541,022 B1 | 4/2003 | Murphy et al. |
| 6,541,037 B1 | 4/2003 | Lee et al. |
| 6,558,307 B2 | 5/2003 | Headley |
| 6,576,015 B2 | 6/2003 | Geistlich et al. |
| 6,586,388 B2 | 7/2003 | Oppermann et al. |
| 6,592,507 B2 | 7/2003 | Jorgensen et al. |
| 6,599,558 B1 | 7/2003 | Al-Lamee et al. |
| 6,613,566 B2 | 9/2003 | Kandler et al. |
| 6,641,552 B1 | 11/2003 | Kingsley et al. |
| 6,649,072 B2 | 11/2003 | Brandt et al. |
| 6,652,473 B2 | 11/2003 | Kaufman et al. |
| 6,663,870 B2 | 12/2003 | Hart et al. |
| 6,710,025 B1 | 3/2004 | Spector |
| 6,739,112 B1 | 5/2004 | Marino |
| 6,743,232 B2 | 6/2004 | Overaker et al. |
| 6,866,991 B2 | 3/2005 | Gilbertson et al. |
| 6,884,428 B2 | 4/2005 | Binette et al. |
| 6,903,078 B1 | 6/2005 | Williams |
| 6,949,251 B2 | 9/2005 | Dalal et al. |
| 6,972,130 B1 | 12/2005 | Lee et al. |
| 6,974,862 B2 | 12/2005 | Ringeisen et al. |
| 7,005,135 B2 | 2/2006 | Janas et al. |
| 7,012,034 B2 | 3/2006 | Heide et al. |
| 7,022,506 B2 | 4/2006 | Brighton et al. |
| 7,041,641 B2 | 5/2006 | Rueger et al. |
| 7,052,518 B2 | 5/2006 | Irie et al. |
| 7,087,540 B2 | 8/2006 | Heide et al. |
| 7,148,209 B2 | 12/2006 | Hoemann et al. |
| 7,192,592 B2 | 3/2007 | Gilbertson et al. |
| 7,192,604 B2 | 3/2007 | Brown et al. |
| 7,250,550 B2 | 7/2007 | Overby et al. |
| 7,357,941 B2 | 4/2008 | Dalal et al. |
| 7,390,498 B2 | 6/2008 | Dalal et al. |
| 7,473,678 B2 * | 1/2009 | Lynch .............................. 514/2 |
| 7,491,384 B2 | 2/2009 | Hart et al. |
| 7,597,883 B2 | 10/2009 | Hart et al. |
| 7,799,754 B2 * | 9/2010 | Hart et al. .................. 424/198.1 |
| 2001/0014662 A1 | 8/2001 | Rueger et al. |
| 2001/0016646 A1 | 8/2001 | Rueger et al. |
| 2001/0016703 A1 | 8/2001 | Wironen et al. |
| 2001/0020188 A1 | 9/2001 | Sander |
| 2001/0038848 A1 | 11/2001 | Donda et al. |
| 2002/0004225 A1 | 1/2002 | Hart et al. |
| 2002/0006437 A1 | 1/2002 | Grooms et al. |
| 2002/0018796 A1 | 2/2002 | Wironen et al. |
| 2002/0022885 A1 | 2/2002 | Ochi |
| 2002/0037799 A1 | 3/2002 | Li et al. |
| 2002/0082220 A1 | 6/2002 | Hoemann et al. |
| 2002/0082694 A1 | 6/2002 | McKay |
| 2002/0098222 A1 | 7/2002 | Wironen et al. |
| 2002/0115647 A1 | 8/2002 | Halvorsen et al. |
| 2002/0120281 A1 | 8/2002 | Overaker |
| 2002/0127265 A1 | 9/2002 | Bowman et al. |
| 2002/0131989 A1 | 9/2002 | Brown et al. |
| 2002/0193883 A1 | 12/2002 | Wironen |
| 2003/0006025 A1 | 1/2003 | Manini et al. |
| 2003/0049328 A1* | 3/2003 | Dalal et al. .................... 424/602 |
| 2003/0055511 A1 | 3/2003 | Schryver et al. |
| 2003/0105015 A1 | 6/2003 | Gilbertson et al. |
| 2003/0109000 A1 | 6/2003 | Moore et al. |
| 2003/0109537 A1 | 6/2003 | Turner et al. |
| 2003/0114936 A1 | 6/2003 | Sherwood et al. |
| 2003/0125252 A1 | 7/2003 | Underhill et al. |
| 2003/0152606 A1 | 8/2003 | Gerber |
| 2003/0180376 A1 | 9/2003 | Dalal et al. |
| 2003/0193106 A1 | 10/2003 | Yu et al. |
| 2003/0199615 A1 | 10/2003 | Chaput et al. |
| 2003/0203002 A1 | 10/2003 | Murphy et al. |
| 2003/0224488 A1 | 12/2003 | Fox et al. |
| 2003/0228364 A1 | 12/2003 | Nathan |
| 2003/0232071 A1 | 12/2003 | Gower et al. |
| 2003/0235622 A1 | 12/2003 | Tas |
| 2004/0002770 A1 | 1/2004 | King et al. |
| 2004/0014727 A1 | 1/2004 | Garrett |
| 2004/0022825 A1 | 2/2004 | Lagow |
| 2004/0033949 A1 | 2/2004 | Bunting et al. |
| 2004/0043031 A1 | 3/2004 | Hart et al. |
| 2004/0064194 A1 | 4/2004 | Irie et al. |
| 2004/0076685 A1 | 4/2004 | Tas |
| 2004/0078077 A1 | 4/2004 | Binette et al. |
| 2004/0078090 A1 | 4/2004 | Binette et al. |
| 2004/0197311 A1 | 10/2004 | Brekke et al. |
| 2004/0224027 A1 | 11/2004 | Spiro et al. |
| 2004/0228870 A9 | 11/2004 | Hart et al. |
| 2004/0230303 A1 | 11/2004 | Gomes et al. |
| 2004/0243133 A1 | 12/2004 | Materna |
| 2004/0265350 A1 | 12/2004 | Sambrook et al. |
| 2005/0027367 A1 | 2/2005 | Heide et al. |
| 2005/0031694 A1 | 2/2005 | Gilbertson et al. |
| 2005/0074481 A1 | 4/2005 | Brekke et al. |
| 2005/0098915 A1 | 5/2005 | Long et al. |
| 2005/0107162 A1 | 5/2005 | Kilby et al. |
| 2005/0107887 A1 | 5/2005 | Knothe Tate et al. |
| 2005/0119754 A1 | 6/2005 | Trieu et al. |
| 2005/0169893 A1 | 8/2005 | Koblish et al. |
| 2005/0170012 A1 | 8/2005 | Dalal et al. |
| 2005/0177203 A1 | 8/2005 | Brighton et al. |
| 2005/0187162 A1 | 8/2005 | Dhanaraj et al. |
| 2006/0029578 A1 | 2/2006 | Hoemann et al. |
| 2006/0084602 A1 | 4/2006 | Lynch |
| 2006/0149392 A1 | 7/2006 | Hsieh et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154367 A1 | 7/2006 | Kihm et al. |
| 2006/0177475 A1 | 8/2006 | Rueger et al. |
| 2006/0190043 A1 | 8/2006 | Brighton et al. |
| 2006/0198939 A1 | 9/2006 | Smith et al. |
| 2006/0205652 A1 | 9/2006 | Zamora et al. |
| 2006/0233853 A1 | 10/2006 | Remington et al. |
| 2006/0247156 A1 | 11/2006 | Vanderby et al. |
| 2006/0292198 A1 | 12/2006 | Dalal et al. |
| 2007/0003752 A1 | 1/2007 | Bruce et al. |
| 2007/0026044 A1 | 2/2007 | Bunting et al. |
| 2007/0048381 A1 | 3/2007 | Hart et al. |
| 2007/0053951 A1 | 3/2007 | Gonzalez Santos et al. |
| 2007/0129807 A1 | 6/2007 | Lynch et al. |
| 2007/0160681 A1 | 7/2007 | Park et al. |
| 2007/0190101 A1 | 8/2007 | Yang et al. |
| 2007/0191851 A1 | 8/2007 | Ashammakhi |
| 2007/0207185 A1 | 9/2007 | Hart et al. |
| 2007/0218098 A1 | 9/2007 | Reif et al. |
| 2007/0244484 A1 | 10/2007 | Luginbuehl |
| 2007/0259018 A1 | 11/2007 | McKay |
| 2007/0259814 A1 | 11/2007 | Lynch |
| 2007/0260326 A1 | 11/2007 | Williams et al. |
| 2007/0282455 A1 | 12/2007 | Luginbuehl et al. |
| 2008/0027470 A1 | 1/2008 | Hart et al. |

| | | | |
|---|---|---|---|
| 2009/0074753 A1 | 3/2009 | Lynch | |
| 2009/0092674 A2 | 4/2009 | Ingram et al. | |
| 2009/0130173 A1 | 5/2009 | Behnam et al. | |
| 2009/0232890 A1 | 9/2009 | Lynch et al. | |
| 2010/0151025 A1 | 6/2010 | Lynch et al. | |
| 2010/0174368 A1 | 7/2010 | Lynch et al. | |
| 2010/0183515 A1 | 7/2010 | Hart et al. | |
| 2010/0196347 A1 | 8/2010 | Kery et al. | |
| 2010/0247651 A1 | 9/2010 | Kestler et al. | |

FOREIGN PATENT DOCUMENTS

| | | | |
|---|---|---|---|
| EP | 0 479 799 B1 | | 4/1992 |
| EP | 0 530 804 A1 | | 3/1993 |
| EP | 0 530 804 B1 | | 3/1993 |
| EP | 0 741 785 B1 | | 11/1996 |
| EP | 0 741 785 B2 | | 11/1996 |
| EP | 0 896 825 A1 | | 2/1999 |
| EP | 0 896 825 B1 | | 2/1999 |
| EP | 0 994 694 B1 | | 4/2000 |
| EP | 1 025 871 A1 | | 8/2000 |
| EP | 1 100 488 B1 | | 5/2001 |
| EP | 1 146 897 B1 | | 10/2001 |
| EP | 1 234 552 A1 | | 8/2002 |
| EP | 1 234 552 B1 | | 8/2002 |
| EP | 1 242 129 B1 | | 9/2002 |
| EP | 1 374 857 A1 | | 1/2004 |
| EP | 1 410 811 A1 | | 4/2004 |
| EP | 1 410 811 B1 | | 4/2004 |
| EP | 1 464 307 A1 | | 10/2004 |
| EP | 1 464 307 B1 | | 10/2004 |
| EP | 1 561 481 A2 | | 8/2005 |
| EP | 1 561 481 A3 | | 8/2005 |
| EP | 1 563 846 A1 | | 8/2005 |
| EP | 1 681 087 A2 | | 7/2006 |
| EP | 1 681 087 A3 | | 7/2006 |
| EP | 1 712 244 A1 | | 10/2006 |
| EP | 1 719 531 A2 | | 11/2006 |
| EP | 1 719 532 A2 | | 11/2006 |
| GB | 2 367 497 A | | 4/2002 |
| JP | 7-250688 A | | 10/1995 |
| JP | 2003-265592 A | | 9/2003 |
| WO | WO-88/03409 A1 | | 5/1988 |
| WO | WO-91/15231 A1 | | 10/1991 |
| WO | WO-91/18098 A1 | | 11/1991 |
| WO | WO-92/09301 A1 | | 6/1992 |
| WO | WO-92/16181 A2 | | 10/1992 |
| WO | WO-93/00432 A1 | | 1/1993 |
| WO | WO-93/05808 A1 | | 4/1993 |
| WO | WO-93/08825 A1 | | 5/1993 |
| WO | WO-93/09229 A1 | | 5/1993 |
| WO | WO-93/16099 A2 | | 8/1993 |
| WO | WO-93/20859 A1 | | 10/1993 |
| WO | WO-94/01557 A1 | | 1/1994 |
| WO | WO-94/05800 A1 | | 3/1994 |
| WO | WO-94/15949 A1 | | 7/1994 |
| WO | WO-94/15965 A1 | | 7/1994 |
| WO | WO-94/15966 A1 | | 7/1994 |
| WO | WO-94/21681 A1 | | 9/1994 |
| WO | WO-94/22463 A1 | | 10/1994 |
| WO | WO-94/26892 A1 | | 11/1994 |
| WO | WO-94/26893 A1 | | 11/1994 |
| WO | WO-94/28889 A1 | | 12/1994 |
| WO | WO-95/01801 A1 | | 1/1995 |
| WO | WO-95/01802 A1 | | 1/1995 |
| WO | WO-95/07982 A1 | | 3/1995 |
| WO | WO-95/10539 A1 | | 4/1995 |
| WO | WO-95/16035 A2 | | 6/1995 |
| WO | WO-95/16035 A3 | | 6/1995 |
| WO | WO-95/18856 A1 | | 7/1995 |
| WO | WO-95/20967 A1 | | 8/1995 |
| WO | WO-95/28124 A2 | | 10/1995 |
| WO | WO-95/28124 A3 | | 10/1995 |
| WO | WO-95/28950 A1 | | 11/1995 |
| WO | WO-96/01845 A1 | | 1/1996 |
| WO | WO-96/02559 A1 | | 2/1996 |
| WO | WO-96/13226 A1 | | 5/1996 |
| WO | WO-96/16668 A1 | | 6/1996 |
| WO | WO-96/17924 A2 | | 6/1996 |
| WO | WO-96/17924 A3 | | 6/1996 |
| WO | WO-97/13857 A1 | | 4/1997 |
| WO | WO-98/00183 A2 | | 1/1998 |
| WO | WO-98/00183 A3 | | 1/1998 |
| WO | WO-98/40113 A1 | | 9/1998 |
| WO | WO-98/41246 A2 | | 9/1998 |
| WO | WO-98/41246 A3 | | 9/1998 |
| WO | WO-98/51354 A2 | | 11/1998 |
| WO | WO-98/51354 A3 | | 11/1998 |
| WO | WO-99/30726 A1 | | 6/1999 |
| WO | WO-99/38543 A2 | | 8/1999 |
| WO | WO-99/38543 A3 | | 8/1999 |
| WO | WO-99/67289 A1 | | 12/1999 |
| WO | WO-00/04940 A1 | | 2/2000 |
| WO | WO-01/32197 A2 | | 5/2001 |
| WO | WO-01/32197 A3 | | 5/2001 |
| WO | WO-01/35932 A2 | | 5/2001 |
| WO | WO-01/35932 A3 | | 5/2001 |
| WO | WO-01/41822 A1 | | 6/2001 |
| WO | WO-01/57083 A1 | | 8/2001 |
| WO | WO-01/60424 A2 | | 8/2001 |
| WO | WO-01/60424 A3 | | 8/2001 |
| WO | WO-01/66044 A2 | | 9/2001 |
| WO | WO-01/66044 A3 | | 9/2001 |
| WO | WO-01/66130 A1 | | 9/2001 |
| WO | WO-01/68135 A2 | | 9/2001 |
| WO | WO-01/68135 A3 | | 9/2001 |
| WO | WO-02/00244 A2 | | 1/2002 |
| WO | WO-02/00244 A3 | | 1/2002 |
| WO | WO-02/00272 A2 | | 1/2002 |
| WO | WO-02/00272 A3 | | 1/2002 |
| WO | WO-02/36147 A1 | | 5/2002 |
| WO | WO-02/062405 A2 | | 8/2002 |
| WO | WO-02/062405 A3 | | 8/2002 |
| WO | WO-02/067978 A1 | | 9/2002 |
| WO | WO-02/070029 A2 | | 9/2002 |
| WO | WO-02/070029 A3 | | 9/2002 |
| WO | WO-02/102783 A1 | | 12/2002 |
| WO | WO-03/006025 A1 | | 1/2003 |
| WO | WO-03/043576 A2 | | 5/2003 |
| WO | WO-03/043576 A3 | | 5/2003 |
| WO | WO-03/065996 A2 | | 8/2003 |
| WO | WO-03/065996 A3 | | 8/2003 |
| WO | WO-03/070186 A2 | | 8/2003 |
| WO | WO-03/070186 A3 | | 8/2003 |
| WO | WO-03/071997 A1 | | 9/2003 |
| WO | WO-2004/002539 A2 | | 1/2004 |
| WO | WO-2004/002539 A3 | | 1/2004 |
| WO | WO-2004/002539 C1 | | 1/2004 |
| WO | WO-2004/010907 A1 | | 2/2004 |
| WO | WO-2004/071543 A1 | | 8/2004 |
| WO | WO-2004/073563 A2 | | 9/2004 |
| WO | WO-2004/073563 A3 | | 9/2004 |
| WO | WO-2004/110308 A2 | | 12/2004 |
| WO | WO-2004/110308 A3 | | 12/2004 |
| WO | WO-2004/110308 C2 | | 12/2004 |
| WO | WO-2005/009496 A1 | | 2/2005 |
| WO | WO-2005/032461 A2 | | 4/2005 |
| WO | WO-2005/032461 A3 | | 4/2005 |
| WO | WO-2005/042048 A2 | | 5/2005 |
| WO | WO-2005/042048 A3 | | 5/2005 |
| WO | WO-2005/046746 A1 | | 5/2005 |
| WO | WO-2005/054279 A1 | | 6/2005 |
| WO | WO-2005/054279 C1 | | 6/2005 |
| WO | WO-2005/072656 A1 | | 8/2005 |
| WO | WO-2006/031388 A2 | | 3/2006 |
| WO | WO-2006/031388 A3 | | 3/2006 |
| WO | WO-2006/034365 A2 | | 3/2006 |
| WO | WO-2006/034365 A3 | | 3/2006 |
| WO | WO-2006/044334 A2 | | 4/2006 |
| WO | WO-2006/044334 A3 | | 4/2006 |
| WO | WO-2006/050493 A2 | | 5/2006 |
| WO | WO-2006/050493 A3 | | 5/2006 |
| WO | WO-2006/093808 A1 | | 9/2006 |
| WO | WO-2006/133403 A2 | | 12/2006 |
| WO | WO-2006/133403 A3 | | 12/2006 |
| WO | WO-2007/061889 A2 | | 5/2007 |
| WO | WO-2007/061889 A3 | | 5/2007 |
| WO | WO-2007/087436 A2 | | 8/2007 |
| WO | WO-2007/087436 A3 | | 8/2007 |

| WO | WO-2007/089997 | A2 | 8/2007 |
| --- | --- | --- | --- |
| WO | WO-2007/089997 | A3 | 8/2007 |
| WO | WO-2007/090102 | A2 | 8/2007 |
| WO | WO-2007/090102 | A3 | 8/2007 |
| WO | WO-2007/092622 | A2 | 8/2007 |
| WO | WO-2007/092622 | A3 | 8/2007 |
| WO | WO-2008/005427 | A2 | 1/2008 |
| WO | WO-2008/005427 | A3 | 1/2008 |
| WO | WO-2008/073628 | A2 | 6/2008 |
| WO | WO-2008/073628 | A3 | 6/2008 |
| WO | WO-2008/103690 | A2 | 8/2008 |
| WO | WO-2008/103690 | A3 | 8/2008 |
| WO | WO-2008/151193 | A1 | 12/2008 |
| WO | WO-2009/100454 | A1 | 8/2009 |
| WO | WO-2010/030714 | A2 | 3/2010 |
| WO | WO-2010/071857 | A1 | 6/2010 |
| WO | WO-2010/102266 | A1 | 9/2010 |

OTHER PUBLICATIONS

Akita, S. et al. (2004). "Capillary Vessel Network Integration by Inserting a Vascular Pedicle Enhances Bone Formation in Tissue-Engineered Bone Using Interconnected Porous Hydroxyapatite Ceramics," *Tissue Eng.* 10(5/6):789-795.

Almojaly, S. (2008). "The Effect of Bisphosphonate, Alendronate, on Primary Human Alveolar Bone Cells," *Masters Abstracts International* 46(6):61.

American Dental Association (Jun. 2006). *Expert Panel Recommendations: Dental Management of Patients on Oral Bisphosphonate Therapy, Report of the Council of Scientific Affairs*, 14 pages.

Anitua, E. et al. "Autologous platelets as a source of proteins for healing and tissue regeneration," *Thromb Haemost*, 2004, 91:4-15.

Anitua et al. (2005). "Autologous Preparations Rich in Growth Factors Promote Proliferation and Induce VEGF and HGF Production by Human Tendon Cells in Culture," *Journal of Orthopaedic Research* 23:281-286.

Anonymous (2003). "The European Market for Dental Bone Graft Substitutes," *Implant Dentistry* 12(1):3-5.

Antoniades, H.N. et al. (May 27, 1983). "Human Platelet-Derived Growth Factor (PDGF): Amino-Terminal Amino Acid Sequence," *Science* 220:963-965.

Antoniades, H.N. et al. (1985). "Platelet-Derived Growth Factor: A Link to Malignant Transformation," in *Cancer Cells 3: Growth Factors and Transformations*, Fermasico, J. et al. eds., Cold Spring Harbor Laboratory: Cold Spring Harbor, NY, 3:145-151.

Antoniades, H.N. et al. (1991). "Molecular Mechanism of Tissue Repair: Injury Induces Expression of PDGF-B and its Receptor," Abstract No. 2156, *J. Dental Res.* 70:536.

Anusaksathien et al. "Growth Factor Delivery to Re-Engineer Periodontal Tissues," *Current Pharmaceutical Biotechnology*, 2002, vol. 3(2):129-139.

Anusaksathien et al. "Platelet-Derived Growth Factor Gene Delivery Stimulates ex Vivo Gingival Repair," *Tissue Engineering*, 2003, 9(4):745-758.

Anusaksathien et al. "Effect of Sustained Gene Delivery of Platelet-Derived Growth Factor or Its Antagonist (PDGF-1308) on Tissue-Engineered Cementum," *J. Periodontal*, Mar. 2004, 75(3):429-440.

Arm, D.M. et al. "Effect of Controlled Release of Platelet-derived Growth Factor from a Porous Hydroxyapatite Implant on Bone Ingrowth," *Biomaterials*, 1996, 17(7):703-709.

Assael, L.A. (2006). "A Time for Perspective on Bisphosphonates," *J. Oral Maxillofac. Surg.* 64:877-879.

Babbush, C.A. DDS MSCD et al. "An In Vitro and In Vivo Evaluation of Autologous Platelet Concentrate in Oral Reconstruction," *Implant Dent.*, 2003, 12(1):24-34.

Barker, K. et al. (Jun. 2006). "Bisphosphonate-Associated Osteonecrosis of the Jaws: A Guide for the General Dental Practitioner," *Dental Update* pp. 270-275.

Basa, S. et al. (2004). "Alternative Bone Expansion Technique for Immediate Placement of Implants in the Edentulous Posterior Mandibular Ridge: A Clinical Report," *International Journal of Oral & Maxofacial Implants* 19(4):554-558.

Bateman, J. et al. "Platelet-Derived Growth Factor Enhancement of Two Alloplastic Bone Matrices," *J. Periodontol.* (Nov. 2005) 76(11):1833-1841.

Becker. W. et al. (Nov. 1992). "A Comparison of PTFE Membranes Alone or in Combination with Platelet-Derived Growth Factor and Insulin-Like Growth Factor-I, or Demineralized Freeze Dried Bone in Promoting Bone Formation Around Immediate Extraction Socket Implants: A Study in Dogs," *J. Periodtonol.* 63(11):929-940.

Berlemann, U. et al. (2002). "Adjacent Vertebral Failure After Vertebroplasty," *J. Bone Joint Surg. BR* 84(B):748-752.

Betsholtz, C. et al. (Apr. 24, 1986). "cDNA Sequence and Chromosomal Localization of Human Platelet-Derived Growth Factor A-Chain and its Expression in Tumour Cell Lines," *Nature* 320:695-699.

Biomimetic Therapeutics (Aug. 21, 2002). "Orthovita and BioMimetic Enter into a Supply Agreement," located at <http://biomimetics.com/cgi-bin/aw/acuweb.cgi?s=biomimetics&t=pressreleasedtl.htm&StoryID=82&>, last visited on May 18, 2010, 6 pages.

Biomimetic Therapeutics (May 21, 2003). "BioMimetic Pharmaceuticals, Inc. Closes Series B Venture Funding," located at <http://biomimetics.com/cgi-bin/aw/acuweb.cgi?s=biomimetics&t=pressreleasedtl.htm&StoryID=76&>, last visited on May 18, 2010, 5 pages.

Biomimetic Therapeutics (Feb. 12, 2004). "BioMimetic Pharmaceuticals Announces Additions to Senior Management Team," located at <http://biomimetics.com/cgi-bin/aw/acuweb.cgi?s=biomimetics&t=pressreleasedtl.htm&StoryID=83&>, last visited on May 18, 2010, 6 pages.

Biomimetic Therapeutics (Jul. 15, 2004). "BioMimetic Pharmaceuticals' Receives Approvable Recommendation from FDA Advisory Panel for GEM 21S®," located at <http://biomimetics.com/cgi-bin/aw/acuweb.cgi?s=biomimetics&t=pressreleasedtl.htm&StoryID=78&>, last visited on May 18, 2010, 6 pages.

Biomimetic Therapeutics (Nov. 4, 2004). "BioMimetic Pharmaceuticals Raises $25.7 Million in Series C Financing," located at <http://biomimetics.com/cgi-bin/aw/acuweb.cgi?s=biomimetics&t=pressreleasedtl.htm&StoryID=79&>, last visited on May 20, 2010, 5 pages.

Biomimetic Therapeutics (May 18, 2005). "BioMimetic Pharmaceuticals Raises Additional $11.8 Million in Equity Financing," located at <http://biomimetics.com/cgi-bin/aw/acuweb.cgi?s=biomimetics&t=pressreleasedtl.htm&StoryID=80&>, last visited on May 18, 2010, 6 pages.

Biomimetic Therapeutics (Jul. 13, 2005). "BioMimetic Pharmaceuticals Strengthens Senior Leadership Team," located at <http://biomimetics.com/cgi-bin/aw/acuweb.cgi?s=biomimetics&t=pressreleasedtl.htm&StoryID=81&>, last visited on May 20, 2010, 6 pages.

Biomimetic Therapeutics (Nov. 21, 2005). "BioMimetic Therapeutics Announces FDA Approval of *GEM 21S®* Growth-Factor Enhanced Matrix for the Treatment of Periodontally-Related Bone Defects," located at <http://biomimetics.com/cgi-bin/aw/acuweb.cgi?s=biomimetics&t=pressreleasedtl.htm&StoryID=87&>, last visited on May 18, 2010, 6 pages.

Biomimetic Therapeutics (Mar. 20, 2006). "BioMimetic Therapeutics Initiates Trials with Novel Bio-Active Drug-Device Combination Bone Graft in Two Orthopedic Indications," located at <http://biomimetics.com/cgi-bin/aw/acuweb.cgi?s=biomimetics&t=pressreleasedtl.htm&StoryID=118&>, last visited on May 18, 2010, 6 pages.

Biomimetic Therapeutics (Jun. 7, 2006). "BioMimetic Therapeutics Receives Approval to Market GEM 21S® Growth-Factor Enhanced Matrix in Canada," located at <http://www.biomimetics.com/cgi-bin/acuweb/acuweb.cgi?s=biom&t=NewsDetail.htm&StoryID=166&>, 5 pages.

Biomimetic Therapeutics (Jul. 11, 2006). "BioMimetic Therapeutics Successfully Completes Enrollment in Three Orthopedic Pilot Clinical Trials for GEM OS1™ Bone Graft; Canadian Study Expanded to 60 Patients," located at <http://biomimetics.com/cgi-bin/aw/acuweb.cgi?s=biomimetics&t=pressreleasedtl.htm&StoryID=93&>, last visited on May 18, 2010, 6 pages.

Biomimetic Therapeutics (Sep. 14, 2006). "BioMimetic Therapeutics' Clinical Investigators to Receive Award from American Academy of Periodontolgy for Outstanding Publication; Clinical Investigators to Present Data at Annual AAP Meeting," located at <http:// biomimetics.com/cgi-bin/aw/acuweb.cgi?s=biomimetics &t=pressreleasedtl.htm&StoryID=94&>, last visited on May 18, 2010, 6 pages.
Biomimetic Therapeutics (Sep. 27, 2006). "BioMimetic Therapeutics Adds Key Talent to Board of Directors," located at <http://biomimetics.com/cgi-bin/aw/acuweb.cgi?s=biomimetics &t=pressreleasedtl.htm&StoryID=97&>, last visited on May 20, 2010, 6 pages.
Biomimetic Therapeutics (Nov. 6, 2006). "BioMimetic Therapeutics' Clinical Investigator Highlights Results of Orthopedic Clinical Trial Canada," located at <http://biomimetics.com/cgi-bin/aw/acuweb.cgi?s=biomimetics&t=pressreleasedtl.htm&StoryID=101& >, last visited on May 18, 2010, 7 pages.
Biomimetic Therapeutics (Dec. 13, 2006). "BioMimetic Therapeutics Announces Positive Results; GEM OS1 Stimulates Bone Healing Comparable to Autograft," located at <http://biomimetics.com/cgi-bin/aw/acuweb.cgi?s=biomimetics&t=pressreleasedtl.htm &StoryID=104&>, last visited on May 18, 2010, 7 pages.
Biomimetic Therapeutics (Jan. 25, 2007). "BioMimetic Therapeutics Reports Positive Clinical Results Using GEM OS® 1 to Treat Distal Radius Fractures," located at <http://biomimetics.com/cgi-bin/aw/acuweb.cgi?s=biomimetics&t=pressreleasedtl.htm&StoryID=105 &>, last visited on May 18, 2010, 6 pages.
Biomimetic Therapeutics (Feb. 21, 2007). "BioMimetic Therapeutics Receives Orphan Drug Designation for rhPDGF-BB Treatment of Osteonecrosis of the Jaw," located at <http://biomimetics.com/cgi-bin/aw/acuweb.cgi?s=biomimetics&t=pressreleasedtl.htm& StoryID=112&>, last visited on Apr. 5, 2010, 6 pages.
Biomimetic Therapeutics (Mar. 28, 2007). "BioMimetic Therapeutics Reports 2006 Fourth Quarter and Year-End Results; Company Receives Clearance to Initiate Enrollment in GEM OS1 US Pivotal Trial," located at <http://biomimetics.com/cgi-bin/aw/acuweb.cgi?s=biomimetics&t=pressreleasedtl.htm&StoryID=113&>, last visited on May 18, 2010, 8 pages.
Biomimetic Therapeutics (May 10, 2007). "BioMimetic Therapeutics to Report 2007 First Quarter Financial Results on May 14," located at <http://biomimetics.com/cgi-bin/aw/acuweb.cgi?s=biomimetics&t=pressreleasedtl.htm&StoryID=111&>, last visited on May 18, 2010, 4 pages.
Biomimetic Therapeutics (May 14, 2007). "BioMimetic Therapeutics Reports 2007 First Quarter Results; Company Added to Nasdaq Biotechnology Index," located at <http://biomimetics.com/cgi-bin/aw/acuweb.cgi?s=biomimetics&t=pressreleasedtl.htm &StoryID=116&>, last visited on May 18, 2010, 7 pages.
Biomimetic Therapeutics (Jun. 7, 2007). "BioMimetic Therapeutics Initiates Enrollment in E.U. Registration Trial for GEM OS® 1 Bone Graft; U.S. GEM OS1 Pivotal Study Protocol Amended to Allow Shorter Follow-Up Time and More Patients," located at <http://biomimetics.com/cgi-bin/aw/acuweb.cgi?s=biomimetics& t=pressreleasedtl.htm&StoryID=119&>, last visited on May 18, 2010, 6 pages.
Biomimetic Therapeutics (Jul. 13, 2007). "BioMimetic Therapeutics' Clinical Investigator Presents Positive Interim Data on U.S. and Canadian Foot and Ankle Clinical Trials," located at <http://biomimetics.com/cgi-bin/aw/acuweb.cgi?s=biomimetics& t=pressreleasedtl.htm&StoryID=123&>, last visited on May 18, 2010, 8 pages.
Biomimetic Therapeutics (Aug. 14, 2007). "BioMimetic Therapeutics Reports 2007 Second Quarter Results," located at <http://biomimetics.com/cgi-bin/aw/acuweb.cgi?s=biomimetics& t=pressreleasedtl.htm&StoryID=125&>, last visited on May 18, 2010, 7 pages.
Biomimetic Therapeutics (Nov. 13, 2007). "BioMimetic Therapeutics Reports 2007 Third Quarter Results," located at <http://biomimetics.com/cgi-bin/aw/acuweb.cgi?s=biomimetics& t=pressreleasedtl.htm&StoryID=127&>, last visited on May 18, 2010, 7 pages.
Biomimetic Therapeutics (Dec. 13, 2007). "BioMimetic Therapeutics reports Positive Clinical Results for GEM OS® 1 in Canadian Foot and Ankle Fusion Study; Clinical Success Rate of 90% Achieved in High Risk Patient Population," located at <http://biomimetics.com/cgi-bin/aw/acuweb.cgi?s=biomimetics& t=pressreleasedtl.htm&StoryID=131&>, last visited on May 18, 2010, 6 pages.
Biomimetic Therapeutics (Dec. 17, 2007). "BioMimetic Therapeutics to Sell Remaining Dental Business for Additional $40 Million Cash Plus Continuation of Royalties; Company to Focus on Orthopedics, Spine and Sports Medicine," located at <http://biomimetics.com/cgi-bin/aw/acuweb.cgi?s=biomimetics&t=pressreleasedtl.htm &StoryID=149&>, last visited on May 18, 2010, 7 pages.
Biomimetic Therapeutics (Feb. 29, 2008). "BioMimetic Therapeutics, Inc. to Highlight Clinical and Preclinical Activities at ORS and AAOS Meetings," located at http://biomimetics.com/cgi-bin/aw/acuweb.cgi?s=biomimetics&t=pressreleasedtl.htm&StoryID=136 &>, last visited on May 18, 2010, 6 pages.
Biomimetic Therapeutics (Mar. 7, 2008). "BioMimetic Therapeutics, Inc. Provides Updates on Clinical and Preclinical Activities; Company Receives Go Ahead from Health Canada to File GEM OS1 DLA," located at <http://biomimetics.com/cgi-bin/aw/acuweb.cgi?s=biomimetics&t=pressreleasedtl.htm&StoryID=138&>, last visited on May 18, 2010, 6 pages.
Biomimetic Therapeutics (Mar. 12, 2008). "BioMimetic Therapeutics Reports 2007 fourth Quarter and Year-End Results; Year Marked by Strong Cash Position, Positive Orthopedic Data and Progressing Clinical Trials," located at <http://biomimetics.com/cgi-bin/aw/acuweb.cgi?s=biomimetics&t=pressreleasedtl.htm&StoryID=137 &>, last visited on May 18, 2010, 8 pages.
Biomimetic Therapeutics (Aug. 11, 2008). "BioMimetic Therapeutics Reports 2008 Second Quarter Results; Positive Results Achieved with Augment™ Injectable Bone Graft to Enhance Healing in Foot and Ankle Fusions," located at <http://biomimetics.com/cgi-bin/aw/acuweb.cgi?s=biomimetics&t=pressreleasedtl.htm&StoryID=151 &>, last visited on May 18, 2010, 8 pages.
Biomimetic Therapeutics (Sep. 23, 2008). "BioMimetic Therapeutics Announces No Changes Requested by Independent Data Monitoring Committee to Pivotal Trial Design for Augment™ Bone Graft; 268 of 396 Patients Enrolled to Date in U.S. Pivotal Trial," located at <http://biomimetics.com/cgi-bin/aw/acuweb.cgi?s=biomimetics& t=pressreleasedtl.htm&StoryID=153&>, last visited on May 18, 2010, 7 pages.
Biomimetic Therapeutics (Oct. 29, 2008). "BioMimetic Therapeutics Reports Promising Clinical Results Using Augment Injectable Bone Graft to Treat Distal Radius Fractures; Enrollment in North American Augment Pivotal Trial Accelerates; 314 of 396 Patients Enrolled," located at <http://biomimetics.com/cgi-bin/aw/acuweb.cgi?s=biomimetics&t=pressreleasedtl.htm&StoryID=159&>, last visited on May 18, 2010, 6 pages.
Biomimetic Therapeutics (Nov. 10, 2008). "BioMimetic Therapeutics Reports 2008 Third Quarter Results," located at <http://biomimetics.com/cgi-bin/aw/acuweb.cgi?s=biomimetics &t=pressreleasedtl.htm&StoryID=157&>, last visited on May 18, 2010, 8 pages.
Biomimetic Therapeutics (Nov. 21, 2008). "BioMimetic Therapeutics, Inc. Announces Patent Allowance from the United Stats Patent and Trademark Office for PDGF Compositions Patent; Expanded Protection for Augment™, Augment™ Injectable and GEM 21S™ Until 2024," located at <http://biomimetics.com/cgi-bin/aw/acuweb.cgi?s=biomimetics&t=pressreleasedtl.htm&StoryID=163&>, last visited on May 18, 2010, 5 pages.
Biomimetic Therapeutics (Dec. 11, 2008). "BioMimetic Therapeutics, Inc. Achieves Patient Enrollment Target (396) in North American Pivotal Study for Augment™ Bone Graft," located at <http://biomimetics.com/cgi-bin/aw/acuweb.cgi?s=biomimetics& t=pressreleasedtl.htm&StoryID=169&>, last visited on May 18, 2010, 5 pages.
Biomimetic Therapeutics (Jan. 7, 2009). "BioMimetic Therapeutics, Inc. Closes Enrollment with 436 Patients in North American Pivotal Study for Augment™ Bone Graft; Company Will File Modular PMA with the FDA Beginning This Spring," located at <http://biomimetics.com/cgi-bin/aw/acuweb.cgi?s=biomimetics&t=pressreleasedtl. htm&StoryID=168&>, last visited on May 18, 2010, 5 pages.
Biomimetic Therapeutics (Feb. 19, 2009). "BioMimetic Therapeutics, Inc. to Highlight Pre-Clinical and Clinical Activities at ORS and AAOS Meetings; Company to Host an Analyst and Investor Meeting Feb. 26," located at <http://biomimetics.com/cgi-bin/aw/acuweb. cgi?s=biomimetics&t=pressreleasedtl.htm&StoryID=154&>, last visited on May 18, 2010, 6 pages.

Biomimetic Therapeutics (Mar. 12, 2009). "BioMimetic Therapeutics Reports 2008 Fourth Quarter and Year End Results," located at <http://biomimetics.com/cgi-bin/aw/acuweb.cgi?s=biomimetics &t=pressreleasedtl.htm&StoryID=160&>, last visited on May 18, 2010, 11 pages.

Biomimetic Therapeutics (May 7, 2009). "BioMimetic Therapeutics Releases 2009 First Quarter Financial Results," located at <http://biomimetics.com/cgi-bin/aw/acuweb.cgi?s=biomimetics& t=pressreleasedtl.htm&StoryID=167&>, last visited on May 18, 2010, 8 pages.

Biomimetic Therapeutics (Aug. 10, 2009). "BioMimetic Therapeutics Reports 2009 Second Quarter Earnings Results," located at <http://biomimetics.com/cgi-bin/aw/acuweb.cgi?s=biomimetics &t=pressreleasedtl.htm&StoryID=185&>, last visited on May 18, 2010, 8 pages.

Biomimetic Therapeutics (Oct. 13, 2009). "BioMimetic Announces Positive Top-Line Data from its Augment Bone Graft North American Pivotal Trial; Augment Demonstrates Non-Inferiority to Autograft," located at < http://biomimetics.com/cgi-bin/aw/acuweb. cgi?s=biomimetics&t=pressreleasedtl.htm&StoryID=188&>, last visited on May 18, 2010, 8 pages.

Biomimetic Therapeutics (Nov. 3, 2009). "BioMimetic Therapeutics Receives First Orthopedic Marketing Approval for Augment Bone Graft," located at <http://biomimetics.com/cgi-bin/aw/acuweb. cgi?s=biomimetics&t=pressreleasedtl.htm&StoryID=190&>, last visited on May 18, 2010, 6 pages.

Biomimetic Therapeutics (Nov. 5, 2009). "BioMimetic Therapeutics Reports 2009 Third Quarter Earnings Results; Company's Second Orthopedic Product Candidate Enters Pivotal Trial for Foot and Ankle Fusion Indications," located at <http://biomimetics.com/cgi-bin/aw/acuweb.cgi?s=biomimetics&t=pressreleasedtl.htm &StoryID= 191 &>, last visited on May 18, 2010, 8 pages.

Biomimetic Therapeutics (Feb. 1, 2010). "BioMimetic Therapeutics, Inc. Patent Portfolio Further Strengthened" located at <http:// biomimetics.com/cgi-bin/aw/acuweb.cgi?s=biomimetics& t=pressreleasedtl.htm&StoryID=199&>, last visited on May 18, 2010, 5 pages.

Biomimetic Therapeutics (Mar. 4, 2010). "BioMimetic Therapeutics, Inc. to Highlight Pre-Clinical and Clinical Activities at ORS and AAOS Meetings; Company to Host Analyst and Investor Meeting on Mar. 11," located at <http://biomimetics.com/cgi-bin/aw/acuweb. cgi?s=biomimetics&t=pressreleasedtl.htm&StoryID=201&>, last visited on May 18, 2010, 6 pages.

Biomimetic Therapeutics (Mar. 9, 2010). "BioMimetic Therapeutics Presents Promising Pre-Clinical Sports Medicine data at the 2010 ORS Meeting," located at <http://biomimetics.com/cgi-bin/aw/ acuweb.cgi?s=biomimetics&t=pressreleasedtl.htm&StoryID=202 &>, last visited on May 18, 2010, 6 pages.

Biomimetic Therapeutics (Mar. 11, 2010). "BioMimetic Therapeutics Reports 2009 Fourth Quarter and Year End Earnings Results; Company Releases Additional Pivotal Data on Augment," located at <http://biomimetics.com/cgi-bin/aw/acuweb.cgi?s=biomimetics &t=pressreleasedtl.htm&StoryID=203&>, last visited on May 18, 2010, 11 pages.

Biomimetic Therapeutics (Mar. 12, 2010). "Morningstar® Document ResearchSM Form 10-K," United States Securities and Exchange Commission Annual Report, located at <http://investor. biomimetics.com/phoenix.zhtml?c=196896&p=irol-sec>, last visited on May 19, 2010, 247 pages.

Björkenheim, J.M. (1989). "Structure and Function of the Rabbit's Supraspinatus Muscle After Resection of its Tendon," *Acta Orthop. Scand.* 60(4):461-463.

Boileau, P. et al. (Jun. 2005). "Arthroscopic Repair of Full-Thickness Tears of the Supraspinatus: Does the Tendon Really Heal?" *J. Bone Joint Surg. Am.* 87-A(6):1229-1240.

Bolander, "Regulation of Fracture Repair by Growth Factors," *P.S. E.B.M.*, 1992, 200:165-170.

Bonfini, T. et al. (Jan. 1, 2006). "Autologous Marrow and Platel Gel in Bone Tissue Regeneration," *Cytotherapy* 8(1), Abstract No. 239, 2 pages.

Bora, F.W. Jr. et al. (Aug. 1987). "Joint Physiology, Cartilage Metabolism, and the Etiology of Osteoarthritis," *Hand Clin.* 3(3):325-336.

Boyden, E.M. et al. (Aug. 1995). "Late Versus Early Repair of Achilles Tendon Rupture: Clinical and Biomechanical Evaluation," *Clin. Orthop. Relat. Res.* 317:150-158.

Braddock, M. et al. (Oct. 2001). "Born Again Bone: Tissue Engineering for Bone Repair," *News Physiool. Sci.* 16:208-213.

Buser, D. et al. (1991). "Effects of Growth Factors on Bone Regeneration Around Titanium Implants," Abstract No. 282, *J. Dental Res.* 70:301.

Business Wire. (Dec. 15, 2000). "Orthovita Recieves U.S. FDA Clearance for VITOSS Scaffold, the First Engineered 90% Porous Beta-Tricalcium Phosphate; Another Milestone Achievement This Year for Orthovita," located at <http://www.highbeam.com/doc/ 1G1-68027113.html>, last visited on Apr. 26, 2010, 3 pages.

Business Wire (May 29, 2002). "Orthovita Issued Patent for Biomaterials Platform Designed to Facilitate Natural Mechanism of Action in Bone Healing," located at <http://www.highbeam.com/ doc/1G1-86413645.html>, last visited on Jun. 17, 2010, 3 pages.

Camargo et al. "Platelet-rich Plasma and Bovine Porous Bone Mineral Combined with Guided Tissue Regeneration in the Treatment of Intrabony Defects in Humans," *J Periodont Res* 2002, 37:300-306.

Camargo, L.V. PM et al. "Effectiveness of a Combination of Platelet-Rich Plasma, Bovine Porous Bone Mineral and Guided Tissue Regeneration in the Treatment of Mandibular Grade II Molar Furcations in Humans," *J. Clin. Periodontol*, 2003, 30:746-751.

Camelo et al. "Clinical, radiographic, and histologic evaluation of human periodontal defects treated with bio-oss and bio-guide," *International Journal of Periodontics and Restorative Dentistry*, 1998, 18(4):321-332.

Camelo et al. "Periodontal regeneration with an autogenous bone-bio-oss composite graft and a bio-guide membrane," *International Journal of Periodontics and Restorative Dentistry.* 2001, 21(2):109-120.

Camelo, M. et al. (Nov. 3, 2003). "Periodontal Regeneration in Human Class II Furcations Using Purified Recombinant Human Platelet-Derived Growth Factor-BB (rhPDGF-BB) with Bone Allograft," *International Journal of Periodontics & Restorative Dentistry* 23(3):213-225.

Canalis, "Effect of Growth Factors on Bone Cell Replication and Differentiation," *Clinical Orthopedics and Related Research*, Mar. 1985, 193:246-263.

Carpio, L. et al. (Nov. 2000). "Guided Bone Regeneration Around Endosseous Implants with Anorganic Bovine Bone Material. A Randomized Controlled Trial Comparing Bioabsorbable Versus Non-Resorbable Barriers," *J. Periodontol.* 71(1):1743-1749.

Catalano, L. et al. (2006). "Bisphoshonates and Risk of Osteonecorisis of the Jaws," *Haema* 9(3):410-414.

Cenni, E. et al. (2003, e-pub. Oct. 1, 2003). "Plasma Levels of Coagulation Inhibitors, Fibrinolytic Markers and Platelet-Derived Growth Factor-AB in Patients with Failed Hip Prosthesis," *Acta Orthop. Scand.* 74(5):559-564.

Cenni, E. et al. (2005, e-pub. Feb. 1, 2005). "Plasma Levels of Platelet-Derived Growth Factor BB and Transforming Growth Factor in Patients with Failed Hip Protheses," *Acta Orthopaedica* 76(1):64-66.

Chen et al. "Adenoviral Gene Transfer of PDGF Downregulates Gas Gene Product PDGFR and Prolongs ERK and AktIPKB Activation," *Am J Physiol Cell Physiol.*, Mar. 2002, 282:C538-C544.

Chiandussi, S. et al. (2006). "Clinical and Diagnostic Imaging of Bisphosphonate-Associated Osteonecrosis of the Jaws," *Dentomaxillofacial Radiology* 35:236-243.

Chin, M. (1995). "Distraction Osteogenesis in Maxillofacial Surgery," Chapter 9 *in Tissue Engineering: Applications in Maxillofacial Surgery and Periodontics*, Lynch, S.E. et al. eds., Quintessence Publishing, pp. 147-159.

Cho et al. (Jun. 1995). "Platelet Derived Growth Factor—Modulated Guided Tissue Regenerative Therapy," *J. Peridontol.* 66(6):522-530.

Clergeau, L.P. et al. (Feb. 1996). "Healing Response to Anorganic Bone Implantation in Periodontal Intrabony Defects in Dogs Part 1. Bone Regeneration. A Microradiographic Study," *J. Periodontool.* 67(2):140-149.

Cochran et al. "Effects of Platelet-Derived Growth Factor Isoforms on Calcium Release From Neonatal Mouse Calvariae," *Bone*, 1993, 14:53-58.

Coleman, S.H. et al. (Dec. 2003). "Chronic Rotator Cuff Injury and Repair Model in Sheep," *The Journal of Bone and Joint Surgery* 85-A(12):2391-2402.

Collins, T. et al. (Aug. 22, 1985). "Cultured Human Endothelial Cells Express Platelet-Derived Growth Factor B Chain: cDNA Cloning and Structural Analysis," *Nature* 316:748-750.

Convery, F.R. et al. (Jan.-Feb. 1972). "The Repair of Large Osteochondral Defects. An Experimental Study in Horses," *Clin. Orthop. Relat. Res.* 82:253-262.

Cooke et al. "Effect of rhPDGR-BB Delivery on Mediators of Periodontal Wound Repair," *Tissue Engineering*, 2006, 12(6):1441-1450.

Costa, M.A. et al. (Jul. 2006). "Tissue Engineering of Flexor Tendons: Optimization of Tenocyte Proliferation Using Growth Factor Supplementation," *Tissue Eng.* 12(7):1937-1943.

Courneya, J-P. et al. (2010). "Normal and Diseased Primary Human Tenocytes in Response to rhPDGF-BB," Poster No. 1118, *56th Annual Meeting of the Orhopaedic Research Society*, located at <http://www.ors.org/web/Transactions/56/1118.pdf>, last visited on Feb. 23, 2010, 1 page.

Creaney, L. et al. (May 2008, e-pub. Nov. 5, 2007). "Growth Factor Delivery Methods in the Management of Sports Injuries: The State of Play," *Br. J. Sports Med.* 42(5):314-320, Abstract Only.

Curi et al. (Jan. 19, 2007). "Treatment of Avascular Osteonecorsis of the Mandible in Cancer Patients with a History of Bisphosphonate Therapy by Combining Bone Resection and Autologous Platelet-Rich Plasma: Report of 3 Cases," *Journal of Oral and Maxillofacial Surgery* 65(2):349-355.

Dalla-Favera, R. et al. (Nov. 12, 1982). "Chromosomal Localization of the Human Homolog (*c-sis*) of the Simian Sarcoma Virus *onc* Gene," *Science* 218:686-688.

Daniels, T.R. et al. (2008). "Application of rhPDGF-BB in Foot and Ankle Fusion Procedures," Chapter 19 *in Tissue Engineering: Applications in Maxillofacial Surgery and Periodontics*, Second Edition, Lynch, S.E. et al. eds., Quintessence Publishing Co.: Hanover Park, IL, pp. 267-275.

Donnelly, B.P. et al. (Jul. 2006). "Nucleotide Structure of Equine Platelet-Derived Growth Factor-A and -B and Expression in Horses with Induced Acute Tendinitis," *Am. J. Vet. Res.* 67(7):1218-1225, Abstract Only.

Doolittle et al. (Jul. 15, 1983). "Simian Sarcoma Virus *onc* Gene *v-sis*, Is Derived from the Gene (or Genes) Encoding a Platelet-Derived Growth Factor," *Science* 221:275-277.

Duffy, F.J. et al. (Jul. 1995). "Growth Factors and Canine Flexor Tendon Healing: Initial Studies in Uninjured and Repair Models," *The Journal of Hand Surgery* 20A(4):645-649.

Dunn, C.A. et al. (Feb. 2005, e-pub. Nov. 6, 2004). "BMP Gene Delivery for Alveolar Bone Engineering at Dental Implant Defects," *Molecular Therapy* 11(2):294-299.

Easley, M.E. et al. (May 2000). "Isolated Subtalar Arthodesis," *JBJS* 82-A(5):613-624.

Eastell, R. et al. (Mar. 1991). "Classification of Vertebral Fractures," *J. Bone Miner. Res.* 6(3):207-215.

Fagan, M.C. et al. (2008). "Simultaneous Augmentation of Hard and Soft Tissues for Implant Site Preparation Using Recombinant Human Platelet-Derived Growth Factor: A Human Case Report," *Int. J. Periodontics Restorative Dent.* 28(1):37-43.

Farrugia, M.C. et al. (Jan. 2006). "Osteonecrosis of the Mandible or Maxilla Associated with the Use of New Generation Bisphosphonates," *The Laryngoscope* 116:115-120.

Feldman, D. et al. (Sep. 1998). "In a Time of Change, Orthopedics Sector is Marked by New Modalities," *The BBI Newsletter*, located at <http://findarticles.com/p/articles/mi_m3570/is_n9_v21/ai_n27541529>, last visited on Mar. 12, 2009, 2 pages.

Fennis et al. "Mandibular reconstruction: A clinical and radiographic animal study on the use of autogenous scaffolds and platelet-rich plasma," *Int. J. Oral Maxillofac. Surg.*, 2002, 31:281-286.

Fennis et al. "Mandibular reconstruction: A histological and histomorphometric study on the use of autoge-us scaffolds, particulate cortico-cancellous bone grafts and platelet rich plasma in goats," *Int. J. Oral Maxillofac. Surg.*, 2004, 33:48-55.

Ficarra, G. et al. (2005). "Osteonecrosis of the Jaws in Periodontal Patients with a History of Bisphophonates Treatment," *J. Clin. Periodontol.* 32:1123-1128.

Final Office Action mailed on Feb. 7, 2008, for U.S. Appl. No. 11/159,533, filed.

Finkelman, R.D. et al. (1995). "Systematic PDGF ± Alendronate Increases Bone Density in OVX Rats," Abstract No. 1281, *J. Dental Res.* 74:172.

Fontana et al. "Effect of Platelet-Rich Plasma on the Pert-implant Bone Response: An Experimental Study," *Implant Dentistry*, 2004, 13:73-78.

Franco, B. et al. (Jan.-Jun. 2008). "Tissue Engineering Approaches for the Construction of a Completely Autologous Tendon Substitute," *Indian J. Plast. Surg.* 41(1):38-46, 13 pages.

Freedonia (Sep. 2006). "Biocompatible Materials. US Industry Study with Forecasts to 2010 & 2015," Study #2111, located at <http://www.freedoniagroup.com/pdf/2111smwe.pdf>, last visited on Jun. 17, 2010, 8 pages. (Table of Contents Only.).

Fribourg, D. et al. (Oct. 15, 2004). "Incidence of Subsequent Vertebral Fracture After Kyphoplasty," *Spine* 29(20):2270-2276.

Fukui, A. et al. (Sep. 1993). "Isolation and Characterization of Xenopus activin and Follistatin," *Devel. Biol.* 159(1):131-139.

Galatz, L.M. et al. (Feb. 2004). "The Outcome and Repair Integrity of Completely Arthoscopically Repaired Large and Massive Rotator Cuff Tears," *J. Bone Joint Surg. Am.* 86-A(2):219-244.

Gamradt, S.C. et al. (Mar. 2007). "Platelet Rich Plasma in Rotator Cuff Repair," *Tech. In Orthop.* 22(1):26-33.

Garg, A.K. (1995). "Grafting Materials in Repair and Restoration," Chapter 5 *in Tissue Engineering: Applications in Maxillofacial Surgery and Periodontics*, Lynch, S.E. et al. eds., Quintessence Publishing, pp. 83-101.

Garg, "The Use of Platelet-Rich Plasma to Enhance the Success of Bone Grafts Around Dental Implants," *Dental Implantology Update*, Mar. 2000, 11(3):17-21.

Gazielly, D.F. et al. (Jul. 1994). "Functional and Anatomical Results After Rotator Cuff Repair," *Clin. Orthop. Relat. Res.* 304:43-53.

Gelberman, R.H. et al. (Mar. 2007). "The Early Effects of Sustained Platelet-Derived Growth Factor Administration on the Functional and Structural Properties of Repaired Intrasynovial Flexor Tendons: An in vivo Biomechanic Study at 3 Weeks in Canines," *J. Hand Surg. Am.* 32(3):373-379, Abstract Only.

Gerber, C. et al. (May 1994). "Mechanical Strength of Repairs of the Rotator Cuff," *J. Bone Joint Surg. Br.* 76-B(3):371-380.

Gerber, C. et al. (Apr. 2000). "The Results of Repair of Massive Tears of the Rotator Cuff," *J. Bone Joint Surg. Am.* 82-A(4):505-515.

Giannobile, W.V. et al. (1994). "Synergistic Effects of Insulin-Like Growth Factors -I (IGF-I) with Other Growth Factors on Bone Formation in vitro," Abstract No. 831, *J. Dental Res.* 73:205.

Giannobile et al. "Comparison of Canine and Non-Human Primate Animal Models for Periodontal Regenerative Therapy: Results Following a Single Administration of PDGF/IGF-I," *J. Periodontol.*, Dec. 1994, 65(12):1158-1168.

Giannobile, W.V. et al. (Nov. 1995). "Platelet Derived Growth Factor (PDGF) and Insulin-Like Growth Factor (IGF-I) Enhances Periodontal Regeneration in Macaca fascicularis," Abstract No. 28, *Advanced Dental Research* 9(3 Suppl.):29.

Giannobile, W.V. et al. (Jul. 1996). "Comparative Effects of Platelet-Derived Growth Factor and Insulin-Like Growth Factor-I, Individually and in Combination, on Periodontal Regeneration in *Macaca fascicularis*," *J. Periodontal Res.* 31(5):301-312.

Giannobile et al. "Periodontal Tissue Engineering by Growth Factors," *Bone*, Jul. 1996, 19(1), Supplement: 23S-37S.

Giannobile et al. "Non-Coordinate Control of Bone Formation Displayed by Growth Factor Combinations with IGF-I," *J Dent Res*, Sep. 1997, 76(9):1569-1578.

Giannobile et al. "Recombinant Human Osteogenic Protein-1 (OP-1) Stimulates Periodontal Wound Healing in Class III Furcation Defects," *J Periodontol*, Feb. 1998, 69(2):129-137.

Giannobile, "Platelet-Derived Growth Factor (PDGF) Gene Delivery for Application in Periodontal Tissue Engineering," *J Periodontol*, Jun. 2001, 72(6):815-823.

Giannobile, W.V. (2008). "Advances in Gene Therapy for Periodontal Bioengineering," Chapter 3 in *Tissue Engineering: Applications in Maxillofacial Surgery and Periodontics*, Second Edition, Lynch, S.E. et al. eds., Quintessence Publishing Co.: Hanover Park, IL, pp. 37-46.

Gilbertson et al. "Platelet-derived Growth Factor C (PDGF-C), a Novel Growth Factor That Binds to PDGF α and β Receptor," *The Journal of Biological Chemistry*, Jul. 20, 2001, 276(29):27406-27414.

Goutallier, D. et al. (Jul. 1994). "Fatty Muscle Degeneration in Cuff Ruptures: Pre- and Postoperative Evaluation by CT Scan," *Clin. Orthop.* 304:78-83.

Grageda, "Platelet-Rich Plasma and Bone Graft Materials: A Review and a Standardized Research Protocol," *Implant Dentistry*, 2004, 13(4):301-309.

Green et al. "Immunolocalization of platelet-derived growth factor A and B chains and PDGF-α and β-receptors in human gingival wounds," *Journal of Periodontal Research*, 1997, 32(2):209-214.

Gronwald et al. "Cloning and expression of a cDNA coding for the human platelet-derived growth factor receptor: Evidence for more than one receptor class," *Proc. Natl. Acad. Sci. USA*, May 1988, 85:3435-3439.

Hanel, D.P. et al. (Jan. 2002). "Wrist Fractures," *Orthop. Clin. North Am.* 33(1):35-57.

Harryman, D.T. et al. (Aug. 1991). "Repairs of the Rotator Cuff," *J. Bone Joint Surg. Am.* 73-A(7):982-989.

Hart et al. "Synthesis, Phosphorylation, and Degredation of Multiple Forms of the Platelet-derived Growth Factor Receptor Studied Using a Mo-clonal Antibody," *The Journal of Biological Chemistry*, Aug. 5, 1987, 262(22):10780-10785.

Hart et al. "Two Classes of PDGF Receptor Recognize Different Isoforms of PDGF," *Science*, Jun. 1988, 240:1529-1531.

Hart, C.E. et al. "Purification of PDGF-AB and PDGF-BB from Human Platelet Extracts and Identification of All Three PDGF Dimers in Human Platelets," *Biochemistry*, Jan. 9, 1990, 29(1):166-172.

Hattrup, S.J. et al. (1985). "A Review of Ruptures of the Achilles Tendon," *Foot & Ankle* 6(1):34-38.

Hee et al. (2003). "Do Autologous Growth Factors Enhance Transformational Lumbar Interbody Fusion?" *Eur. Spine. J.* 12(4):400-407.

Heini, P.F. et al. (2001, e-pub. Jun. 14, 2001). "Bone Substitutes in Vertebroplasty," *Eur. Spine J.* 10:S205-S213.

Helm et al. (Apr. 2001). "Bone Graft Substitutes for the Promotion of Spinal Arthrodesis," *Neurosur. Foc.* 10(4):1-5.

Higashi, T. et al. (Jun. 1996). "Influence of Particle Size of Calcium Phosphate Ceramics as a Capping Agent on the Formation of a Hard Tissue Barrier in Amputated Dental Pulp," *Journal of Endodontics* 22(6):281-283.

Hoffmann, A. et al. (Dec. 2007, e-pub. Jul. 19, 2007). "Tendon and Ligament Engineering in the Adult Organism: Mesenchymal Stem Cells and Gene-Therapeutic Approaches," *Int. Orthop.* 31(6):791-797.

Hollinger, J.O. et al. (Jan. 2008, e-pub. Aug. 3, 2007). "Accelerated Fracture Healing in the Geriatric Osteoporotic Rat with Recombinant Human Platelet-Derived Growth Factor-BB and an Injectable Beta-Tricalcium Phosphate/Collagen Matrix," *J. Orthopedic Res.* 26:83-90.

Hollinger, J.O. et al. (Feb. 2008). "Recombinant Human Platelet Derived Growth Factor: Biology and Clinical Applications," *J. Bone & Joint Surgery* 90-A(Suppl. 1):48-54.

Hollinger, J.O. et al. (2008). "Therapeutic Opportunities for Bone Grafting," Chapter 68 in *Principles of Regenerative Medicine*, Atala, A. et al. eds., Academic Press: Burlington, MA, pp. 1164-1175.

Hollinger, J.O. et al. (2008). "Protein Therapeutics and Bone Healing," Chapter 1 in *Tissue Engineering: Applications in Maxillofacial Surgery and Periodontics*, Second Edition, Lynch, S.E. et al. eds., Quintessence Publishing Co.: Hanover Park, IL, pp. 3-25.

Hossain, M.Z. et al. (Jul. 1996). "Biological Responses of Autogenous Bone and Beta-Tricalcium Phosphate Ceramics Transplanted into Bone Defects to Orthodontic Forces," *Cleft Palate-Craniofacial Journal* 33(4):277-283.

Howell, T.H. et al. (1996). "Polypeptide Growth Factors for Periodontal Regeneration," *Current Opinion in Periodontology* 3:149-156.

Howell et al. "A Phase I/II Clinical Trial to Evaluate a Combination of Recombinant Human Platelet-Derived Growth Factor-BB and Recombinant Human Insulin-Like Growth Factor-I in Patients with Period. Dis.," *J. Periodontol.*, Dec. 1997, 68(12):1186-1193.

Howes et al. "Platelet-Derived Growth Factor Enhances Demineralized Bone Matrix-Induced Cartilage and Bone Formation," *Calcif Tissue Int.*, 1988, 42:34-38.

Huang, L.-H. et al. "The Effect of Platelet-Rich Plasma on the Coronally Advanced Flap Root Coverage Procedure: A Pilot Human Trial," J. Periodontal, Oct. 2005, 76(10):1768-1777.

Hsu et al. (Jul. 2004). "Clinical Implications of Growth Factors in Flexor Tendon Wound Healing," *The Journal of Hand Surgery* 29A(4):551-563.

Ikezawa et al. "Characterization of Cementum Derived Growth Factor as an Insulin-Like Growth Factor-I Like Molecule," *Connective Tissue Research*, 1997, 36(4):309-319.

Ito, Y. et al. (2004, e-pub. Mar. 26, 2004). "Bone Formation Using Novel Interconnected Porous Calcium Hydroxyapatite Ceramic Hybridized with Cultured Marrow Stromal Stem Cells Derived From Green Rat," *J. Biomed. Mater. Res.* 69A:454-461.

Jensen et al. "Platelet rich plasma and fresh frozen bone allograft as enhancement of implant fixation—An experimental study in dogs," *Journal of Orthopaedic Research*, 2004, 22:653-658.

Jensen, O.T. et al. (2008). "Alveolar Distraction Osteogenesis and Tissue Engineering," Chapter 14 in *Tissue Engineering: Applications in Maxillofacial Surgery and Periodontics*, Second Edition, Lynch, S.E. et al. eds., Quintessence Publishing Co.: Hanover Park, IL, pp. 203-219.

Jensen, O.T. (2008). "Dentoalveolar Modification with an Osteoperiosteal Flap and rhPDGF-BB," Chapter 15 in *Tissue Engineering: Applications in Maxillofacial Surgery and Periodontics*, Second Edition, Lynch, S.E. et al. eds., Quintessence Publishing Co.: Hanover Park, IL, pp. 220-225.

Jiang, D. et al. "Modification of an Osteoconductive Anorganic Bovine Bone Miami Matrix with Growth Factors," *J. Periodonlol.*, Aug. 1999, 70(8):834-839.

Jin et al. "Engineering of Tooth-Supporting Structures by Delivery of PDGF Gene Therapy Vectors," *Molecular Therapy*, Apr. 2004, 9(4):519-526.

Jin, Q. et al. (Mar. 5, 2008). "Nanofibrous Scaffolds Incorporating PDGF-BB Microspheres Induce Chemokine Expression and Tissue Neogenesis In Vivo," *PLoS ONE* 3(3):e1729, pp. 1-9.

Jones et al. (1992). "Isolation of Vgr-2, a Novel Member of the Transforming Growth Factor-Beta-related Gene Family," *Mol Endocnnol.* 6(11):1961-1968.

Jozsa, L. et al. (Aug. 1989). "Fibronectin and Laminin in Achilles Tendon," *Acta Orthop Sacninavica* 60(4):469-471.

Kademani, D. et al. (Aug. 2006). "Primary Surgical Therapy for Osteonecrosis of the Jaw Secondary to Bisphosphonate Therapy," *Mayo Clin. Proc.* 81(8):1100-1103.

Kaigler, "Growth factor delivery for oral and periodontal tissue engineering," *Expert Opin Drug Deliv.*, 2006, 3(5):647-662.

Kapuściński, P. et al. (Jul.-Sep. 1996). "An Analgesic Effect of Synthetic Human Calcitonin in Patients with Primary Osteoporosis," *The Polish Journal of Medicine and Pharmacy* 28(98):83-86.

Kassolis et al. "Alveolar Ridge and Sinus Augmentation Utilizing Platelet-Rich Plasma in Combination with Freeze-Dried Bone Allograft: Case Series," *Journal of Periodontology*, Oct. 2000, 71(10):1654-1661.

Kazlauskas et al. "Different effects of homo- and heterodimers of platelet-derived growth factor A and 8 chains on human and mouse fibroblasts," *The EMBO Journal*(1988) 7 (12):3727-3735.

Kim et al. "A Comparative Study of Osseointegration of Avana Implants in a Demineralized Freeze-Dried Bone Alone or With Platelet-Rich Plasma," *J Oral Maxillofac Surg*, 2002, 60:1018-1025.

Kim et al. "Use of Particulate Dentin-Plaster of Paris Combination with/without Platelet-Rich Plasma in the Treatment of Bone Defects Around Implants," *The International Journal of Oral & Maxillofacial Implants*, 2002; 17:86-94.

Klotzbuecher, C.M. et al. (Apr. 2000). "Patients with Prior Fractures Have an Increased Risk of Future Fractures: A Summary of the Literature and Statistical Synthesis," *J. Bone Miner. Res.* 15(4):721-739.

Kovacevic, D. et al. (Mar. 2008). "Biological Augmentation of Rotator Cuff Tendon Repair," *Clin. Orthop. Relat. Res.* 466(3):622-633.

Kovacs et al. "Comparative Study of b-Tricalcium Phosphate Mixed with Platelet-Rich Plasma versus β-Tricalcium Phosphate, A Bone Substitute Material in Dentistry," *Acts Veterinaria Hungarica*, 2003, 51(4):475-484.

Landesberg et al. "Quantification of Growth Factor Levels Using a Simplified Method of Platelet-Rich Plasma Gel Preparation," *J. Oral Maxillofac. Surg.*, 2000, 58:297-301.

Lasa et al. "Delivery of Demineralized Bone Powder by Fibrin Sealant," *Plast. Reconstr. Surg.*, 1995, 96(6):1409-1417.

Lasa JR., C. et al. (1996). "Bone Induction by Demineralized Bone Powder and Partially Purified Osteogenin Using a Fibrin-Sealant Carrier," Chapter 14 *in Surgical Adhesives and Sealants: Current Technology and Applications*, Sierra, D. et al. eds., Technomic Publishing Company, Inc.: Lancaster, PA, pp. 135-144.

Lee, Y-M. et al. (Mar. 2000). "The Bone Regenerative Effect of Platelet-Derived Growth Factor-BB Delivered With a Chitosan/Tricalcium Phosphate Sponge Carrier," *J. Periodontal.* 71(3):418-424.

Lee, S.J. et al. (2001, e-pub. Feb. 13, 2001). "Molded Porous Poly ($_L$-Lactide) Membranes for Guided Bone Regeneration with Enhanced Effects by Controlled Growth Factor Release," *Journal of Biomedical Materials Research* 55:295-303.

Lee et al. "Enhanced bone formation by controlled growth factor delivery from chitosan-based biomaterials," *Journal of Controlled Release*, 2002, 78: 187-197.

Lekovic, V. et al. (Feb. 2002). "Comparison of Platelet-Rich Plasma, Bovine Porous Bone Mineral, and Guided Tissue Regeneration Versus Platelet-Rich Plasma and Bovine Porous Bone Mineral in the Treatment of Intrabony Defects: A Reentry Study," *J. Periodontol.* 73(2):198-205.

Letson, A.K. et al. (1994). "The Effect of Combinations of Growth Factors on Ligament Healing," *Clinical Orhopaedics and Related Research* 308:207-212.

Li, J. et al. (1994). "Systematic Administration of PDGF With or Without Alendronate Increases Spine and Whole Body Bone Mineral Density in OVX Rats," Abstract No. 59, *Sixteenth Annual Meeting of the American Society for Bone and Mineral Research*, Kansas City, MO. , Sep. 9-13, 1994, p. S135.

Liang et al. (Sep. 2000). "Effect of Cytokines on Repair of Tendon Injury," *Pub Med* 14(5):283-285, Abstract Only.

Liang, H.W. et al. (Aug. 2009). "Effect of Platelet -Derived Growth Factor-BB on Proliferation of Tendon Cells Cultured in vitro," *Zhonghua Shao Shang Za Zhi* 25(4):298-300, Abstract Only.

Lind et al. (1998). "Growth Factor Stimulation of Bone Healing," *Acta Orthopaedica Scandinavica Supplementum* Suppl. 283:2-37.

Lioubavina-Hack et al. "Methyl cellulose gel obstructed bone formation by GBR: an experimental study in rats," *J. Clin. Periodontol.*, 2005, 32:1247-1253.

Lioubavina-Hack et al. "Effect of Bio-Oss® with or without platelet-derived growth factor on bone formation by 'guided tissue regeneration': a pilot study in rats," *J Clin. Periodontol*, 2005, 32(12):1254-1260.

Lipshitz, H. et al. (Jun. 1975). "In Vitro Wear of Cartilage," *J. Bone Joint Surg. Am.* 57A(4):527-534.

Lynch, S.E. et al. (Nov. 1987). "Role of Platelet-Derived Growth Factor in Wound Healing: Synergistic Effects with Other Growth Factors," *Proc. Natl. Acad. Sci. USA* 84:7696-7700.

Lynch, S.E. et al. (1988). "Synergistic Effects of Recombinant Platelet-Derived Growth Factor Two and Insulin-Like Growth Factor-I in Wound Healing," Abstract No. 585, *J. Dental Res.* 67:186.

Lynch, S.E. et al. (1988). "Potential Role of Platelet-Derived and Insulin-Like Growth Factors in Periodontal Regeneration," Abstract No. 586, *J. Dental Res.* 67:186.

Lynch, S.E. et al. (Dec. 1988). "Growth Factors in Wound Healing: Single and Synergistic Effects," Abstract No. 238, *J. Cell Biol.* 107(6 Part 3):46a.

Lynch, S.E. et al. (1989). "Comparative Effects of Growth Factors on Soft Tissue Repair," Abstract No. 1153, *J. Dental Res.* 68:326.

Lynch, S.E. et al. (1989). "A Combination of Platelet-Derived and Insulin-Like Growth Factors Enhances Periodontal Regeneration," *J. Clin. Periodontol.* 16:545-548.

Lynch, S.E. (1990). "A Possible Role for Polypeptide Growth and Differentiation Factors in Periodontal Regeneration," *Executive Committee on Chemotherpeutics; Amer. Acad Peridontal—Position Paper* pp. 1-4.

Lynch, S.E. et al. (Jul. 1991). "The Effects of Short Term Application of a Combination of Platelet-Derived and Insulin-Like Growth Factors on Periodontal Wound Healing," *J. Periodontol.* 62(7):458-467.

Lynch, S.E. et al. (Nov. 1991). "Effects of Platelet-Derived Growth Factor/Insulin Like Growth-Factor-I Combination on Bone Regeneration Around Titanium Dental Implants. Results of a Pilot Study in Beagle Dogs," *J. Periodontol.* 62(11):710-717.

Lynch, S.E. (1991). "Platelet-Derived Growth Factor and Insulin-Like Growth Factor. I: Mediators of Healing Soft Tissue and Bone Wounds," *Periodontol Case Reports NE Soc. Periodontists Bull.* 13(2):13-20.

Lynch, S.E. et al. (1992). "Effect of PDGF-B and IGF-I on Bone Regeneration," Abstract No. 82, *J. Dental Res.* 71:116.

Lynch, S.E. (1993). "Comparison of Results in the Canine and Primate Models Using a Single Regenerative Therapy," Abstract No. 37, *J. Dental Res.* 72:108.

Lynch, S.E. et al. (Jul.-Sep. 1994). "The Combination of Platelet-Derived Growth Factor-BB and Insulin-Like Growth Factor-I Stimulates Bone Repair in Adult Yucatan Miniature Pigs," *Wound Rep. Reg.* 2(3):182-190.

Lynch, S.E. et al. (Jan.-Mar. 1994). "Evidence for a Synergistic Interaction of Platelet-Derived Growth Factor-BB and Insulin-Like Growth Factor-I to Promote bone Repair in Adult Yucatan Micro Pigs," *Wound Repair and Regeneration* Abstract, 2(1):84.

Lynch, S.E. et al. (1994). "Polypeptide Growth Factors: Molecular Mediators of Tissue Repair," Chapter 33 *in Molecular Pathogenesis of Periodontal Disease*, Genco, R. et al eds., A.S.M. Press: Washington DC, pp. 415-425.

Lynch, S.E. (1994). "The Role of Growth Factors in Periodontal Repair and Regeneration," Chapter 11 *in Periodontal Regeneration: Current Status and Directions*, Polson, A. ed. Quintessence Publishing Co, Inc: Chicago, IL, 11:179-197.

Lynch, S.E. (1995). "Introduction," *in Tissue Engineering: Applications in Maxillofacial Surgery and Preiodontics*, Lynch, S.E. et al. eds., Quintessence Publishing, pp. xi-xvi.

Lynch, S.E. (2005). "Bone Regeneration Techniques in the Orofacial Region," Chapter 18 *in Bone Regeneration and Repair: Biology and Clinical Applications*, Lieberman, J.R. et al. eds., Humana Press Inc.: Totowa, NJ, pp. 359-390.

Lynch, S.E. et al. (Dec. 2006). "A New Era in Periodontal and Periimplant Regeneration: Use of Growth-Factor Enhanced Matrices Incorporating rhPDGF," *Compendium of Continuing Education in Dentistry* 27(12):672-679.

Lynch, S.E. et al. (2008). "Use of rhPDGF to Improve Bone and Periodontal Regeneration," Chapter 6 *in Tissue Engineering: Applications in Maxillofacial Surgery and Periodontics*, Second Edition, Lynch, S.E. et al. eds., Quintessence Publishing Co.: Hanover Park, IL, pp. 87-102.

Maiorana et al. "Maxillary Sinus Augmentation with Anorganic Bovine Bone (Bio-Oss) and Autologous Platelet-Rich Plasma: Preliminary Clinical and Histologic Evaluations," *Int J Periodontics Restorative Den*, 2003, 23(3):227-235.

Manske et al. (Feb. 1985). "Flexor Tendon Healing," *Symposium on Flexor Tendon Surgery, Hand Clinics* 1(1):25-34.

Marcopoulou et al. (2003). "Proliferative Effect of Growth Factors TGF-β1, PDGF-BB, and rhBMP-2 on Human Gingival Fibroblasts and Periodontal Ligament Cells," *Journal of International Academy of Periodontology* 5(3):63-70.

Marx, R.E. et al. (2005). "Bisphosphonate-Induced Exposed Bone (Osteonecrosis/Osteoperosis) of the Jaws: Risk Factors, Recognition, Prevention, and Treatment," *J. Oral Maxillofac. Surg.* 63:1567-1575.

Marx, R.E. (2008). "Application of Tissue Engineering Principles to Clinical Practice," Chapter 4 *in Tissue Engineering: Applications in*

*Maxillofacial Surgery and Periodontics*, Second Edition, Lynch, S.E. et al. eds., Quintessence Publishing Co.: Hanover Park, IL, pp. 47-63.

Marx, R.E. (2008). "Use of PRP in Oral and Maxillofacial Surgery and Periodontology," Chapter 9 *in Tissue Engineering: Applications in Maxillofacial Surgery and Periodontics*, Second Edition, Lynch, S.E. et al. eds., Quintessence Publishing Co.: Hanover Park, IL, pp. 132-144.

Mayfield, L. et al. (Oct. 1998). "Clinical and Radiographic Evaluation, Following Delivery of Fixed Reconstructions, at GBR Treated Titanium Fixtures," *Clin. Oral Implants Res.* 9:292-302.

McAllister, B. et al. (1998). "Long-term Evaluation of Sinus Grafting with Bio-Oss® in the Chimpanzee," Abstract No. 1097, *J. Dental Res.* 77:769.

McAllister et al. "Eighteen-month Radiographic and Histologic Evaluation of Sinus Grafting with A-rganic Bovine Bone in the Chimpanzee," *The International Journal of Oral & Maxillofacial Implants*, 1999, 14(3):361-368.

McCarrel, T. et al. (Aug. 2009, e-pub. Jan. 23, 2009). "Temporal Growth Factor Release from Platelet-Rich Plasma, Trehalose Lyophilized Platelets, and Bone Marrow Aspirate and their Effect on Tendon and Ligament Gene Expression," *J. Orthop. Res.* 27(8):1033-1042, Abstract Only.

McGuire, M.K. et al. (2006). "rhPDGF-BB Promotes Healing of Periodontal Defects: 24-Month Clinical and Radiographic Observations," *Int. J. Periodontics Restorative Dent.* 26(3):223-231.

McGuire, M.K. (2008). "Soft Tissue Engineering Applications in Dentistry," Chapter 7 *in Tissue Engineering: Applications in Maxillofacial Surgery and Periodontics*, Second Edition, Lynch, S.E. et al. eds., Quintessence Publishing Co.: Hanover Park, IL, pp. 103-118.

McMurty, R.Y. et al. (1992). "Fractures of the Distal Radius," Chapter 35 *in Skeletal Trauma*, Browner B.D. et al. eds., W.B. Saunders Company: Philadelphia, PA, 2:1063-1094.

Mehta, V. et al. (Apr.-Jun. 2005). "The Use of Growth Factors on Tendon Injuries," *Journal of Hand Therapy* 18:87-92.

Melo, M.D. et al. (Dec. 2005). "Osteonecrosis of the Jaws in Patients with a History of Receiving Bisphosphonate Therapy. Strategies for Prevention and Early Recognition," *J. American Dental Association* 136:16751681.

Migliorati, C.A. et al. (Jun. 2006). "Bisphosphate-Associated Osteonecrosis: A Long Term Complication of Bisphophonate Treatment," *Lancet Oncol.* 7:508-514.

Mitlak et al. "The Effect of Systemically Administered PDGF-BB on the Rodent Skeleton," *Journal of Bone and Mineral Research*, 1996, 11(2):238-247.

Molloy, T. et al. (2003). "The Roles of Growth Factors in Tendon and Ligament Healing," *Sports Med.* 33(5):381-394.

Mont, M.A. et al. (Oct. 1998). "Osteonecrosis of the Femoral Head. Potential Treatment with Growth and Differentiation Factors," *Clin. Orthop. Relat. Res.* 355(Suppl.):S314-S335, Abstract Only, 2 pages.

Morris, G.J. et al. (Jan. 2007). "Bisphosphonate Therapy for Women with Breast Cancer and at High Risk for Osteoporosis," *Journal of the National Medical Association* 99(1):35-45.

Mott, D.A. et al. (2002). "Enhancement of Osteoblast Proliferation in vitro by Selective Enrichment of Demineralized Freeze-Dried Bone Allograft with Specific Growth Factors," *J. Oral Implantol.* 28(2):57-66.

Mumford, J.H. et al. (Mar. 2001). "The Effects of Platelet Derived Growth Factor-BB on Periodontal Cells in In Vitro Wound Model," *J. Periodontal.* 72(3):331-340.

Nakamura, N. et al. (1998). "Early Biological Effect of In Vivo Gene Transfer of Platelet-derived Grown Factor (PDGF)-B into Healing Patellar Ligament," *Gene Therapy* 5:1185-1170.

Nancollas, G.H. et al. (2006, e-pub. Jul. 2005). "Novel Insights into Actions of Bisphosphonates on Bone: Differences in Interactions with Hydrozyapatite," *Bone* 38:617-627.

Nase, J.B. et al. (Aug. 2006). "Osteonecrosis of the Jaw and Oral Bisphosphonate Treatment," *J. American Dental Association* 137:1115-1119.

Nash, T.J. et al. (Mar. 1994). "Effect of Platelet-Derived Growth Factor on Tibial Osteotomies in Rabbits," *Bone* 15(2):203-208.

Nevins, M.L. et al. (2003). "Evaluation of Periodontal Regeneration Following Grafting Intrabony Defects with Bio-Oss® Collagen: A Human Histologic Report," *Int. J. Periodont. Rest. Dent.* 23(1):9-17.

Nevins et al. "Periodontal Regeneration in Humans Using Recombinant Human Platelet-derived Growth Factor-BB (rhPDGF-BB) and Allogenic Bone," J. Periodontal, Sep. 2003, 74(9):1282-1292.

Nevins, M.L. et al. (2005). "Three-Dimensional Micro-Computed Tomographic Evaluation of Periodontal Regeneration: A Human Report of Intrabony Defects Treated with Bio-Oss Collagen," *Int. J. Periodontics Restorative Dent.* 25(4):365-373.

Nevins et al. "Platelet-Derived Growth Factor Stimulates Bone Fill and Rate of Attachment Level Gain: Results of a Large Multicenter Randomized Controlled Trial," *J. Periodontal*, 2005, 76(12):2205-2215.

Nevins, M. et al. (Oct. 2007). "Clinical Results Using Recombinant Human Platelet-Derived Growth Factor and Mineralized Freeze-Dried Bone Allograft in Periodontal Defects," *Int. J. Periodontics Restorative Dent.* 27(5):421-427.

Nevins, M. et al. (2008). "Treatment of Advanced Periodontal Defects Using Bioactive Therapies," Chapter 5 *in Tissue Engineering: Applications in Maxillofacial Surgery and Periodontics*, Second Edition, Lynch, S.E. et al. eds., Quintessence Publishing Co.: Hanover Park, IL, pp. 67-86.

Nevins, M.L. et al. (2008). "Site Development for Implant Placement: Regenerative and Esthetic Techniques in Oral Plastic Surgery," Chapter 8 *in Tissue Engineering: Applications in Maxillofacial Surgery and Periodontics*, Second Edition, Lynch, S.E. et al. eds., Quintessence Publishing Co.: Hanover Park, IL, pp. 119-131.

Nickols, J.C. et al. (2008). "The Role of Growth Factors in Tendon Healing," Chapter 20 *in Tissue Engineering: Applications in Maxillofacial Surgery and Periodontics*, Second Edition, Lynch, S.E. et al. eds., Quintessence Publishing Co.: Hanover Park IL, pp. 276-289.

Nociti, F.H. Jr. et al. (2000). "Histometric Evaluation of Bone Regeneration Around Immediate Implants Partially in Contact with Bone: A Pilot Study in Dogs," *Implant Dentistry* 9(4):321-328.

Oberg, S. et al. (Apr. 1994). "Bone Healing After Implantation of Hydroxyapatite Granules and Blocks (Interpore 200) Combined with Autolyzed Antigen-Extracted Allogeneic Bone and Fibrin Glue. Experimental Studies on Adult Rabbits," *International Journal of Oral and Maxillofacial Surgery* 23(2):110-114, abstract only.

Orbay, J.L. et al. (Jan. 2004). "Volar Fixed-Angle Plate Fixation for Unstable Distal Radius Fractures in the Elderly Patient," *J. Hand Surg.* 29A(1):96-102.

Orthovita, Inc. (Dec. 14, 2000). "510(k) Summary. Vitoss™ Scaffold Syntehtic Cancellous Bone Void Filler," located at <http://www.accessdata.fda.gov/cdrh_docs/pdf/k994337.pdf>, last visited on Mar. 30, 2010, 6 pages.

Orthovita, Inc. (Nov. 19, 2002). "Morningstar® Document Research™. Form 10-Q, Quarterly Repot Which Provides a Continuing View of a Company's Financial Position," located at <http://orthovita.com/investors/secfilings.aspx>, last visited on Jun. 17, 2010, 48 pages.

Orthovita, Inc. (2009). "Architects of the New Biomaterials Age, 2008 Annual Report," located at <http://orthovita.com/investors/annual-reports/previousreports.aspx>, last visited on Jun. 17, 2010, 93 pages.

Owen et al. (1984). "Simian Sarcoma Virus-Transformed Cells Secrete a Mitogen Identical to Platelet-Derived Growth factor," *Science* 25:54-56.

Palti, A. et al. (2002). "A Concept for the Treatment of Various Dental Bone Defects," *Implant Dentistry* 11(1):73-78.

Parashis, A. et al. (Jul. 1998). "Comparison of 2 Regenerative Procedures-Guided Tissue Regeneration and Demineralized Freeze-Dried Bone Allograft—in the Treatment of Intrabony Defects: A Clinical and Radiographic Study," *J. Periodontol.* 69(7):751-758.

Park et al. (1995). "Periodontal Regeneration in Class III Furcation Defects of Beagle Dogs Using Guided Tissue Regenerative Therapy with Platelet-Derived Growth Factor," *J. Periodontol* 66:462-476.

Paul, W. et al. (1999). "Development of Porous Spherical Hydroxyapatite Granules: Application Towards Protein Delivery," *J. Mater. Sci. Mater. Med.* 10:383-388.

Persson, G.R. et al. (2000). "A Retrospective Radiographic Outcome Assessment Study of Intra-Bony Defects Treated by Osseous Surgery or by Bone Graft Procedures," *J. Clin. Periodontol* 27:104-108.

Petersen, W. et al. (Nov. 2003, e-pub. Apr. 16, 2003). "Hypoxia and PDGF Have a Synergistic Effect that Increases the Expression of the Angiogenetic Peptide Vascular Endothelial Growth Factor in Achilles Tendon Fibroblasts," *Arch. Orthop. Trauma Surg.* 123(9):485-488.
Pfeilschifter, J. et al. (Jul.-Dec. 1990). "Stimulation of Bone Matrix Apposition in Vitro by Local Growth Factors: A Comparison Between Insulin-Like Growth Factor I, Platelet Derived Growth Factor, and Transforming Growth Factor," *Endocrinology* 127(1):69-75.
Philippart et al. "Human Recombinant Tissue Factor, Platelet-rich Plasma, and Tetracycline Induce a High-Quality Human Bone Graft A 5-year Survey," *The International Journal of Oral and Maxillofacial Implants*, 2003, 18(3):411-416.
Phillips, S. et al. (1988). "The Direct Medical Costs of Osteoporosis for American Woman Aged 45 and Older, 1986," *Bone* 9(4):271-279.
Pickett, F.A. (Jul. 2006). "Bisphosphonate-Associated Osteonecrosis of the Jaw: A Literature Review and Clinical Practice Guidelines," *Journal of Dental Hygiene* 80(3):1-12.
Pietrzak, W.S. et al. (Jul. 2000). "Calcium Sulfate Bone Void Filler: A Review and a Look Ahead," *J. Craniofac. Surg.* 11(4):327-333; discussion p. 334.
Polverini, P.J. (Aug. 2002). "Angiogenesis in Health and Disease: Insights into Basic Mechanisms and Therapeutic Opportunities," *Journal of Dental Education* 66(8):962-975.
Qiu, Y. et al. (2009). "Combination of PDGF-BB and bFGF Reduces Differentiation but Maintains Proliferation of Human Tenocytes in Low Bovine Serum Culture in vitro," *European Cells and Materials* 18(Suppl. 2):86.
Qu, Z. et al. (Nov. 1994). "Immunolocalization of Basic Fibroblast Growth Factor and Platelet-Derived Growth Factor-A During Adjuvant Arthritis in the Lewis Rat," *Am. J. Pathol.* 145(5):1127-1139.
Rao, C.D. et al. (Apr. 1986). "Structure and Sequence of the Human C-Sis Platelet-Derived Growth Factor 2 (*SIS/PDGF2*) Transcriptional Unit," *Proc. Natl. Acad. Sci. USA* 83:2392-2396.
Rao, M.V. et al. (Mar. 2009). "Effects of Platelet-Derived Growth Factor, Vitamin D and Parathroid Hormone on Osteoblasts Derived from Cancer Patients on Chronic Bisphosphonate Therapy," *Int. J. Mol. Med.* 23(3):407-413, Abstract Only, 2 pages.
Rasubala, L. et al. "Platelet-derived Growth Factor and Bone Morphogenetic Protein in the Healing of Mandibular Fractures in Rats," *British Journal of Oral and Maxillofacial Surgery*, 2003, 41:173-178.
Riley, G. (2004, e-pub. Jul. 16, 2003). "The Pathogenesis of Tendinopathy. A Molecular Perspective," *Rheumatology* 43(2):131-142.
Robbins, K.C. et al. (Oct. 13, 1983). "Structural and Immunological Similarities Between Simian Sarcoma Virus Gene Product(s) and Human Platelet-Derived Growth Factor," *Nature* 305:605-608.
Rodeo, S.A. et al. (Dec. 1993). "Tendon Healing in a Bone Tunnel," *J. Bone Joint Surg. Am.* 75-A(12):1795-1803.
Rodeo, S.A. et al. (1999). "Use of Recombinant Human Bone Morphogenic Protein-2 to Enhance Tendon Healing in a Bone Tunnel," *Am. J. Sports Med.* 27(4):476-488.
Rodriguez et al. "Maxillary Sinus Augmentation with Deproteinated Bovine Bone and Platelet Rich Plasma with Simultaneous Insertion of Endosseous Implants," *J. Oral Maxiilofac. Surg.*, 2003, 61:157-163.
Rohrich et al. (Nov. 1999). "Mersilene Suture as a Vehicle for Delivery of Growth Factors in Tendon Repair," *Journal of the American Society of Plastic Surgeons* 104(6):1713-1717.
Rolf, C.G. et al. (2001). "Increased Cell Proliferation and Associated Expression of PDGFRβ Causing Hypercellularity in Patellar Tendinosis," *Rheumatology* 40:256-261.
Ruggiero, S.L. et al. (2006, e-pub. Jul. 31, 2006). "Bisphosphonate-Related Osteoncerosis of the Jaw: Background and Guidelines for Diagnosis, Staging and Management," *Oral Surgery, Oral Medicine, Oral Pathology, Oral Radiology, and Endodontology* <http://www.sciencedirect.com/science/journal/10792104>, 8 pages.
Ruiz, G. et al. (1991). "Short Term Administration of Growth Factors Enhances Periodontal Regeneration," Abstract No. 1615, *J. Dental Res.* 70:468.
Russell, T.A. et al. (Date Unknown). "Trigen® IM Nail System Surgical Technique. Trochanteric Antegrade Nail (TAN™)," 24 pages.

Rutherford et al. (1992). "Platelet-Derived and Insulin-Like Growth Factors Stimulate Regeneration of Periodontal Attachment in Monkeys," *Journal of Periodontal Research* 27(4-Part 1):285-290.
Sakiyama-Elbert, S.E. et al. (Nov. 2008). "Controlled-Release Kinetics and Biologic Activity of Platelet-Derived Growth Factor-BB for Use in Flexor Tendon Repair," *J. Hand Surg. Am.* 33(9):1548-1557, Abstract Only.
Sandberg, "Matrix in Cartilage and Bone Development: Current Views on the Function and Regulation of Major Organic Components," *Annals of Medicine*, 1991, 23:207-217.
Sarment, D.P. et al. (Feb. 1, 2006). "Effect of rhPDGF-BB on Bone Turnover During Periodontal Repair," *Journal of Clinical Periodontolgy* 33(2):135-140.
Sartori, S. et al. (2003, e-pub. May 20, 2003). "Ten-year Follow-up in a Maxillary Sinus Augmentation Using Anorganic Bovine Bone (Bio-Oss): A Case Report with Histomorphometric Evaluation," *Clin. Oral Implants Res.* 14(3):369-372.
Sasai, Y. et al. (1994). "*Xenopus chordin*: A Novel Dorsalizing Factor Activated by Organizer-Specific Homeobox Genes," *Cell* 79:779-790.
Saygin et al. "Molecular and Cell Biology of Cementum," *Periodontology*, 2000, 24:73-98.
Schenk, R.K. et al. (Jan./Feb. 1994). "Healing Pattern of Bone Regeneration in Membrane-Protected Defects: A Histologic Study in the Canine Mandible," *Int. J. Oral Maxillofac. Implants* 9(1):13-29.
Schmidt, C.C. et al. (Mar. 1995). "Effect of Growth Factors on the Proliferation of Fibroblasts from the Medial Collateral and Anterior Cruciate Ligaments," *J. Orthop. Res.* 13(2):184-190, Abstract Only.
Schmidt et al. "A review of the effects of insulin-like growth factor and platelet derived growth factor on in vivo cartilage healing and repair," *Osteoarthritis and Cartilage*, 2006, 14(5):403-412.
Schmidt, M.B. et al. (2008). "Tissue Engineering Strategies in the Treatment of TMDs," Chapter 18 *in Tissue Engineering: Applications in Maxillofacial Surgery and Periodontics*, Second Edition, Lynch, S.E. et al. eds., Quintessence Publishing Co.: Hanover Park, IL, pp. 252-264.
Schmitt, J.M. et al. (Nov. 1997). "Comparison of Porous Bone Mineral and Biologically Active Glass in Critical-Sized Defects," *J. Periodontol.* 68(11):1043-1053.
Schnabel, L.V. et al. (Feb. 2007). "Platelet Rich Plasma (PRP) Enhances Anabolic Gene Expression Patterns in Flexor Digitorum Superficialis Tendons," *J. Orthop. Res.* 25(2):230-240, Abstract Only.
Secinfo.com (Mar. 31, 2003). "Interpore International Inc/DE 10-K for Dec. 31, 2002," <http://www.secinfo.com/dV179.2kp.htm, last visited on May 20, 2010, 57 pages.
Shahgaldi, B.F. et al. (Jan. 1991). "Repair of Cartilage Lesions Using Biological Implants. A Comparative Histological and Biomechanical Study in Goats," *J. Bone Joint Surg. Br.* 73-B(1):57-64.
Sharma, P. et al. (2008). "Tendinopathy and Tendon Injury: The Future," *Disability and Rehabilitation* 30(20-22):1733-1745.
Sigma (Date Unknown). "Platelet Derived Growth Factor-BB," Product Information Sheet, 2 pages.
Simion, M. et al. (Apr. 1994). "A Comparative Study of the Effectiveness of e-PTFE Membranes With and Without Early Exposure During the Healing Period," *Int. J. Periodontics Restorative Dent.* 14(2):166-180.
Simion, M. et al. (1994). "Vertical Ridge Augmentation Using a Membrane Technique Associated with Osseointegrated Implants," *Int. J. Periodontics Restorative Dent.* 14(6):497-511.
Simion, M. et al. (1995). "Bacterial Penetration in vitro Through GTAM Membrane With and Without Topical Chlorhexidine Application: A Light and Scanning Electron Microscopic Study," *J. Clin. Periodontol.* 22:321-331.
Simion, M. et al. (Feb. 1998). "Vertical Ridge Augmentation Around Dental Implants Using a Membrane Technique and Autogenous Bone or Allografts in Humans," *Int. J. Periodontics Restorative Dent.* 18(1):9-23.
Simion, M. et al. (1999). "Effect of Different Microstructures of e-PTFE Membranes on Bone Regeneration and Soft Tissue Response: A Histologic Study in Canine Mandible," *Clin. Oral Implants Res.* 10:73-84.

Simion, M. et al. (Oct. 2006). "Vertical Ridge Augmentation by Means of Deproteinized Bovine Bone Block and Recombination Human Platelet-Derived Growth Factor-BB: A Histologic Study in a Dog Model," *The International Journal of Periodontics & Restorative Dentistry* 26(5):415-423.

Simion, M. et al. (2008). "Minimally Invasive Strategies for Vertical Ridge Augmentation," Chapter 10 in *Tissue Engineering: Applications in Maxillofacial Surgery and Periodontics*, Second Edition, Lynch, S.E. et al. eds., Quintessence Publishing Co.: Hanover Park, IL, pp. 145-158.

Siris, E.S. et al. (Aug. 2006). "Adherence to Bisphosphonate Therapy and Fracture Rates in Osteoporotic Women: Relationship to Vertebral and Nonvertebral Fractures From 2 US Claims Databases," *Mayo Clin. Proc.* 81(8):1013-1022.

Solheim, E. "Growth Factors in Bone," *International Orthopedics (SICOT)*, 1998, 22:410-416.

Spector, M. (2008). "Basic Principles of Scaffolds in Tissue Engineering," Chapter 2 in *Tissue Engineering: Applications in Maxillofacial Surgery and Periodontics*, Second Edition, Lynch, S.E. et al. eds., Quintessence Publishing Co.: Hanover Park, IL, pp. 26-36.

Spindler, K.P. et al. (1995). "Proliferative Response to Platelet-Derived Growth Factor in Young and Old Rat Patellar Tendon," *Connective Tissue Research* 31(2):171-177.

Spindler, K.P. et al. (Jul. 1996). "Patellar Tendon and Anterior Cruciate Ligament Have Different Mitogenic Responses to Platelet-Derived Growth Factor and Transforming Growth Factor β," Journal of Orthopaedic Research 14(4):542-546.

Stephan, E.B. et al. (Apr. 1999). "Anogranic Bovine Bone Supports Osteoblastic Cell Attachment and Proliferation," *J. Periodontol.* 70(4):364-369.

Stephan et al. "Platelet-Derived Growth Factor Enhancement of a Mineral-Collagen Bone Substitute," *J. Periodontal*, Dec. 2000, 71:1887-1892.

Strom, T.B. (Sep. 6, 2005). "Saving Islets from Allograft Rejection," *PNAS USA* 102(36):12651-12652.

Suba et al. "Facilitation of β-Tricalcium Phosphate-Induced Alveolar Bone Regeneration by Platelet-Rich Plasma in Beage Dogs: A Histologic and Histomorphometric Study," *The International J. of Oral and Maxillofacial Implants*, 2004, 19(6):832-838.

Tadic, D. et al. (2004). "A Novel Method to Produce Hydroxyapatite Objects with Interconnecting Porosity that Avoids Sintering," *Biomaterials* 25(16):3335-3340.

Tamai, N. et al. (2002). "Novel Hydroxyapatite Ceramics with an Interconnective Porous Structure Exhibit Superior Osteoconduction in vivo," *J. Biomed. Mater. Res.* 59:110-117.

Teraoka, K. et al. (2004). "Construction of an Interconnected Pore Network Using Hydroxyapatite Beads," *Key. Eng. Mater.* 254-256:257-259.

Teraoka, K. et al. (Sep. 2004). "Construction of Interconnected Pore Network Using Hydroxyapatite Small Components," *Trans. Mater. Res. Soc. Jpn.* 29(6):2919-2921.

Thompoulos, S. et al. (May 2005). "Effect of Several Growth Factors on Canine Flexor Tendon Fibroblast Proliferation and Collagen Synthesis in vitro," *J. Hand Surg. Am.* 30(3):441-447, Abstract Only.

Thomopoulos, S. et al. (Oct. 2007, e-pub. Jun. 5, 2007). "PDGF-BB Released in Tendon Repair Using a Novel Delivery System Promotes Cell Proliferation and Collagen Remodeling," *J. Orthop. Res.* 25(17):1358-1368.

Thomopoulos, S. et al. (Sep. 2009, e-pub. Mar. 25, 2009). "Enhanced Flexor Tendon Healing through Controlled Delivery of Pdgf-BB," *J. Orthop. Res.* 27(9):1209-1215, Abstract Only.

Thomopoulos, S. et al. (Feb. 2010, e-pub. Nov. 24, 2009). "bFGF and PDGF-BB for Tendon Repair: Controlled Release and Biologic Activity by Tendon Fibroblasts In Vitro," *Ann. Biomed. Eng.* 38(2):225-234.

Tinti, C. et al. (1996). "Vertical Ridge Augmentation: What is the Limit?" *Int. J. Periodontics Restorative Dent.* 16(3):221-229.

Van Den Wyngaert, T. et al. (Aug. 2006). "Bisphosphonates and Osteonecrosis of the Jaw: Cause and Effect or a *post hoc* Fallacy?" *Annals of Oncology* 17(8):1197-1204.

Venkatasatya, M. et al. (2008). *The Effect of PDGF, Vitamin D and PTH on Osteoblasts Derived From Patients on Chronic Bisphosphonate Therapy*, Dissertation for The State University of New York at Buffalo, located at <http://gradworks.umi.com/14/531/1453440.html>, last visited on Mar. 31, 2010, 2 pages, Abstract Only.

Virchenko, O. et al. (2008, e-pub. Jul. 4, 2008). "Early Achilles Tendon Healing in Sheep," *Arch. Orthop. Trauma Surg.* 128:1001-1006.

Visnapuu et al. "Distribution of fibroblast growth factors (FGFR-1 and -3) and platelet-derived growth factor receptors (PDGFR) in the rat mandibular condyle during growth," *Orthod. Craniofadal.* 2002, 5:147-153.

Walter, C. et al. (2006, e-pub. Aug. 29, 2006). "Prevalence of Bisphophonate Associated Osteonecrosis of the Jaw within the Filed of Osteonecrosis," *Support Care Center* 6 pages.

Wang, Y. et al. (Feb. 23, 1996). "A Large Family of Putative Transmembrane Receptors Homologous to the Product of the Drosophila Tissue Polarity Gene Frizzled," *J. Biol. Chem.* 271(8):4468-4476.

Wang, L. et al. (2004). "Three-Dimensional Porous Network Structure Developed in Hydroxyapatite-Based Nanocomposites Containing Enzyme Pretreated Silk Fibronin," *J. Nanopart.* 6(1):91-98.

Wang, X.T. et al. (Sep. 2004). "Tendon Healing In Vitro: Genetic Modification of Tenocytes With Exogenous PDGF Gene and Promotion of Collagen Gene Expression," *The Journal of Hand Surgery* 29A(5):884-890.

Warner, J.J.P. et al. (Jan. 1992). "Anatomy and Relationships of the Suprascapular Nerve: Anatomical Constraints to Mobalization of the Supraspinauts and Infraspinatus Muscles in the Management of Massive Rotator-Cuff Tears," *J. Bone Joint Surg. Am.* 74-A(1):36-45.

Wei et al. "Nano-Fibrous Scaffold for Controlled Delivery of Recombinant Human PDGF-BB," *Journal of Controlled Release*, 2006, e-pub. Mar. 3, 2006, 112:103-110.

White, E. et al. (1986). "Biomaterial Aspects of Interpore-200 Porous Hydroxyapatite," *Dent. Clin. North Am.* 30(1):49-67, Abstract only.

Wiesen, R.J. et al. (1998). "Efficacy of Bovine Bone Mineral in Vertical Osseous Defects," Abstract No. 1165, *J. Dental Res.* 77:777.

Wikesjö et al. (1988). "Repair of Periodontal Furcation Defects in Beagle Dogs Following Reconstructive Surgery Including Root Surface Demineralization with Tetracycline Hydrochloride and Topical Fibronectin Application," *J. Clin. Periodontol* 15:73-79.

Wikesjö et al. (1989). "Effects of Subgingival Irrigation on *A. actinomycetemcomitans*," *J. Clin. Perrodont.* 16:116-119.

Williams et al. "Tissue Engineering: What Does It Mean? Why Is It Important?" *Compendium*, Jan. 2005, 26(1):54-60.

Wisner-Lynch, L.A. (Oct. 2006). "From Passive to Active: Will Recombinant Growth Factor Therapeutics Revolutionize Regeneration?" *Int. J. Periodont. and Rest. Dent.* 26(5):409-411.

Wong, M.W. et al. (Oct. 2003). "Effect of Dexamethasone on Cultured Human Tenocytes and its Reversibility by Platelet-Derived Growth Factor," *Journal of Bone and Joint Surgery American* 85-A(10)1914-1920, Abstract Only.

Woo, S.L-Y. et al. (1998). "Engineering the Healing of the Rabbit Medical Collateral Ligament," *Medical and Biological Engineering and Computing* 36:359-364.

Woo, S-B. et al. (May 16, 2006). "Systematic Review: Bisphosphonates and Osteonecrosis of the Jaws," *Annals of Internal Medicine* 144(10):753-761.

Yang, C. et al. (2003). "Vascular Endothelial Growth Factor Gene Transfection to Enhance the Repair of Avascular Necrosis of the Femoral Head of Rabbit," *Chinese Medical Journal* 116(10):1544-1548.

Yazawa et al. "Basic Studies on the Clinical Applications of Platelet-Rich Plasma," *Cell Transplantation*, 2003, 12:509-518.

Yazawa, M. et al. (May 2004). "Basic Studies on the Bone Formation Ability by Platelet Rich Plasma in Rabbits," *Journal of Craniofacial Surgery* 15(3):439-446.

Yokota, K. et al. (2008, e-pub. Feb. 1, 2008). "Platelet-Rich Plasma Accelerated Surgical Angio-Genesis in Vascular Necrotic Bone. An Experimental Study in Rabbits," *Acta Orhopaedica* 79(1):106-110.

Younger, E.M. et al. (1989). "Morbidity at Bone Graft Donor Sites," *J. Orthop. Trauma* 3(3):192-195.

Zavras, A.I. et al. (2006). "Bisphosphonated are Associated With Increased Risk for Jaw Surgery in Medical Claims Data: Is it Osteonecrosis?" *J. Oral Maxillofac. Surg.* 64:917-923.

Zhu et al. "Gene Transfer and Expression of Platelet-Derived Growth Factors Modulate Periodontal Cellular Activity," *J. Dent Res*, 2001, 80(3):892-897.

Premdas, J. et al. (2001). "The Presence of Smooth Muscle Action in Fibroblasts in the Torn Human Rotator Cuff," *Journal of Orthopaedic Research* 19:221-238.

Gelberman, R.H. et al. (Mar. 2007). "The Early Effects of Sustained Platelet-Derived Growth Factor Administration on the Functional and Structural Properties of Repaired Intrasynovial Flexor Tendons: An In Vivo Biomechanic Study at 3 Weeks in Canines," *J. Hand Surg. Am.* 32A(3):373-379.

Hollinger, J.O. (2007). "Enhanced Fracture Healing in the Geriatric-Osteoporotic Rat with Recombinant Human Platelet-Derived Growth Factor Homodimer BB (rhPDGF-BB) and Collagen/β-Tricalcium Phosphate Matrix," Poster No. 0930, *53rd Annual Meeting of the Orhopaedic Research Society*, San Diego, CA, located at <http://www.ors.org/web/Transactions/53/0930.PDF>, last visited on Mar. 22, 2011, 1 page.

Perrien, D.S. et al. (2008). "Percutaneous Injection of GEMOS® 2, a Cobmination of rhPDGF-BB and Bovine Type I Collagen/βTricalcium Phosphate (βTCP) Matrix Increases Vertebral Bone Minearl Density in Geriatric Female Baboons," Poster No. 963, *54th Annual Meeting of the Orthopaedic Research Society*, San Francisco, CA, located at <http://www.ors.org/web/Transactions/54/0963.PDF>, last visited on Mar. 22, 2011, 1 page.

Young, C.S. et al. (2007). "Bone Toxicology Study of Recombinant Human Platelet-Derived Growth Factor-BB (rhPDGF-BB) Injected Locally at the Metatarsus and Femur of Rats," Poster No. 1550, *53rd Annual Meeting of the Orhopaedic Research Society*, San Diego, CA, located at <http://www.ors.org/web/Transactions/53/1550.PDF>, last visited on Mar. 22, 2011, 1 page.

\* cited by examiner

COMPOSITIONS AND METHODS FOR ARTHRODETIC PROCEDURES

CROSS-REFERENCE TO RELATED APPLICATIONS

This application is a National Phase filing under 35 U.S.C. §371 of International Application No. PCT/US2007/083638, filed on Nov. 5, 2007, which claims the benefit of the filing date of U.S. Provisional Patent Application No. 60/856,588, filed Nov. 3, 2006, the entire contents of which are incorporated herein by reference in their entirety.

FIELD OF THE INVENTION

The present invention relates to compositions and methods useful for arthrodetic procedures and for promoting fusion of bones in a joint.

BACKGROUND OF THE INVENTION

Musculoskeletal problems are pervasive throughout the population in all age groups and in both sexes. Half of Americans will need services for fractures or bone fusions at some point in their lifetime according to a widely published article presented at the 2003 annual meeting of the American Academy of Orthopedic Surgeons (AAOS). More than $10 billion per year is spent in the United States on hospital care associated with fracture treatment according to this article.

In many cases, arthrodetic procedures are used to treat musculoskeletal problems associated with various joints of patients. Arthrodetic procedures and arthrodesis, as used herein, refer to the surgical immobilization of a joint resulting from fusion of bones of the joint. Arthrodesis of the foot and ankle is a commonly utilized procedure for the treatment of multiple etiologies of foot and ankle pathology, including post-traumatic arthritis, inflammatory arthropathy, seronegative arthropathy, significant joint instability, suboptimal alignment and/or pain. Midfoot, hindfoot, and ankle fusion procedures, such as the triple (three hindfoot articulations), subtalar, talonavicular, and ankle fusions involve the treatment principles of taking down any residual cartilage to the subchondral surface at the level of the involved joint without disturbing its anatomy, stabilizing the joint thereafter with rigid fixation, placing autograft bone (harvested locally or from iliac crest) or other appropriate fusion preparation into surrounding interstices and defects across the joint surface, followed by a relatively standard post-operative regimen of short term immobilization, physical therapy, and gradually increasing load on the fusion site(s).

The time to healing after fusion procedures is longer than that after more conservative treatment methods due to the time required for fusion/union. Historically, an average of two to three months are needed to achieve complete bony union and full weight bearing (FWB) status after these operations. Nonunion rates of other midfoot, hindfoot, and ankle fusion procedures (0-40%) may be higher than those cited for the forefoot. The literature consensus on non-union rates associated with foot and ankle procedures is approximately 10% (See, e.g., Easley et al., Isolated Subtalar Arthrodesis, JBJS, 82-A(5), 2000 pp. 613-624). Nonunions will be detected by 4 and 8 months radiographically and are generally clinically well established by 6-9 months (hence the clinically accepted standard of 4-5 months without evidence of bony progression to declare delayed union and 9 months for declaring nonunion).

Arthrodetic procedures, including arthrodesis of the foot and ankle, often utilize autologous bone grafts to facilitate sufficient bone healing. Autologous bone grafts are widely used due to the fact that there is no risk of cross-contamination associated with allografts or xenografts. Clinical difficulties, nevertheless, exist with autologous bone grafts. Most of these difficulties result from the harvest of the bone graft, including increased operative time, hospital stay and cost, increased blood loss, post-operative pain, risk of infection and/or fracture. Other reported complications associated with autograft include a potential nidus for infection associated with avascular bone, limited tissue supply, and variability in cellular activity of the bone graft (See e.g., Morbidity at bone graft donor sites, J Orthop Trauma 1989, 3, pp. 192-195). In addition to these complications, there is a limited amount of bone graft that may be harvested for use as a bone void filler.

In view of the difficulties associated with autologous bone grafts, it would be desirable to provide alternative osteogenic regeneration systems. It would additionally be desirable to provide methods of using alternative osteogenic regeneration systems in bone fracture treatments and arthrodetic procedures, including foot and ankle arthrodesis.

SUMMARY

The present invention provides compositions and methods for use in arthrodetic procedures. These compositions and methods promote fusion of bones in a joint. In accordance with embodiments of the present invention, there are provided compositions and methods for use in arthrodetic procedures, such as arthrodetic procedures of the foot and ankle. The present compositions and methods facilitate the healing response in arthrodetic procedures including bony union at fusion sites.

The present invention additionally provides for the use of compositions of the present invention in the preparation of an implant material useful for the fusion of bones in a joint. The present invention additionally provides for the use of compositions of the present invention in the preparation of a medicament useful for the fusion of bones in a joint.

In one aspect, a composition provided by the present invention for promoting the fusion of bone in an arthrodetic procedure comprises a solution comprising platelet derived growth factor (PDGF) and a biocompatible matrix, wherein the solution is disposed or incorporated in the biocompatible matrix. In some embodiments, the PDGF is absorbed by the biocompatible matrix. In other embodiments, the PDGF is adsorbed onto one or more surfaces of the biocompatible matrix. In a further embodiment, the PDGF is absorbed by the biocompatible matrix and adsorbed onto surfaces of the biocompatible matrix.

In some embodiments, PDGF is present in the solution in a concentration ranging from about 0.01 mg/ml to about 10 mg/ml, from about 0.05 mg/ml to about 5 mg/ml, from about 0.1 mg/ml to about 1.0 mg/ml or from about 0.2 mg/ml to about 0.4 mg/ml. The concentration of PDGF within the solution may be within any of the concentration ranges stated above.

In embodiments of the present invention, PDGF comprises PDGF homodimers and heterodimers, including PDGF-AA, PDGF-BB, PDGF-AB, PDGF-CC, PDGF-DD, and mixtures and derivatives thereof. In one embodiment, PDGF comprises PDGF-BB. In another embodiment PDGF comprises a recombinant human (rh) PDGF such as rhPDGF-BB.

In embodiments of the present invention, PDGF comprises PDGF fragments. In one embodiment rhPDGF-B comprises the following fragments: amino acid sequences 1-31, 1-32, 33-108, 33-109, and/or 1-108 of the entire B chain. The complete amino acid sequence (1-109) of the B chain of PDGF is provided in FIG. 15 of U.S. Pat. No. 5,516,896. It is to be understood that the rhPDGF compositions of the present invention may comprise a combination of intact rhPDGF-B (1-109) and fragments thereof. Other fragments of PDGF may be employed such as those disclosed in U.S. Pat. No. 5,516,896. In accordance with a preferred embodiment, the rhPDGF-BB comprises at least 65% of intact rhPDGF-B (1-109).

The present invention provides a composition for promoting the fusion of two or more bones in an arthrodetic procedure comprising a PDGF solution disposed in a biocompatible matrix, wherein the biocompatible matrix comprises a bone substituting agent (also called a bone scaffolding material herein) and optionally a biocompatible binder. Exemplary bone substituting agents include, e.g., a calcium phosphate (e.g., tricalcium phosphate (e.g., β-TCP), hydroxyapatite, poorly crystalline hydroxyapatite, amorphous calcium phosphate, calcium metaphosphate, dicalcium phosphate dihydrate, heptacalcium phosphate, calcium pyrophosphate dihydrate, calcium pyrophosphate, and octacalcium phosphate), calcium sulfate, or demineralized bone (e.g., demineralized freeze-dried cortical or cancellous bone)). The PDGF solution may have any concentration of PDGF as described herein. A bone scaffolding material, in some embodiments, comprises calcium phosphate. In one embodiment, calcium phosphate comprises β-TCP. In some embodiments, biocompatible matrices may include calcium phosphate particles with or without biocompatible binders or bone allograft such as demineralized freeze dried bone allograft (DFDBA) or particulate demineralized bone matrix (DBM). In another embodiment, biocompatible matrices may include bone allograft such as DFDBA or DBM.

Moreover, a biocompatible binder, according to some embodiments of the present invention, comprises proteins, polysaccharides, nucleic acids, carbohydrates, synthetic polymers, or mixtures thereof. In one embodiment, a biocompatible binder comprises collagen. In another embodiment, a biocompatible binder comprises hyaluronic acid.

In another aspect, the present invention provides a kit for use in arthrodetic procedures comprising a biocompatible matrix in a first package and a solution comprising PDGF in a second package. In some embodiments, the solution comprises a predetermined concentration of PDGF. The concentration of the PDGF can be predetermined according to requirements of the arthrodetic procedure(s) being performed. Moreover, in some embodiments, the biocompatible matrix can be present in the kit in a predetermined amount. In some embodiments, the biocompatible matrix in the kit comprises a bone scaffolding material, a bone scaffolding material and a biocompatible binder, and/or bone allograft such as DFDBA or particulate DBM. In one embodiment, the bone scaffolding material comprises a calcium phosphate, such as β-TCP. In one embodiment, the binder comprises collagen. The amount of biocompatible matrix provided by a kit relates to requirements of the arthrodetic procedure(s) being performed. In some embodiments, the second package containing the PDGF solution comprises a syringe. A syringe can facilitate disposition of the PDGF solution in or on the biocompatible matrix for application at a surgical site, such as a site of bone fusion in an arthrodetic procedure. In some embodiments, once the PDGF solution has been incorporated into the biocompatible matrix, the resulting composition is placed in a second syringe and/or cannula for delivery to a site of desired bone fusion in a joint. Alternatively, the composition may be applied to the desired site with another application means, such as a spatula, spoon, knife, or equivalent device.

The present invention additionally provides methods for producing compositions for use in arthrodetic procedures as well as methods of performing arthrodetic procedures. In one embodiment, a method for producing a composition comprises providing a solution comprising PDGF, providing a biocompatible matrix, and disposing or incorporating the PDGF solution in the biocompatible matrix.

In another embodiment, a method of performing an arthrodetic procedure comprises providing a composition comprising a PDGF solution disposed in a biocompatible matrix and applying the composition to a site of desired bone fusion in a joint. In some embodiments, a method of performing an arthrodetic procedure comprises applying the composition to at least one site of desired bone fusion in a plurality of joints. Applying the composition to a site of desired bone fusion, in some embodiments, comprises injecting the composition in the site of desired bone fusion.

In some embodiments, a method of performing an arthrodetic procedure comprises surgically accessing a site of desired bone fusion in a joint, incorporating a composition comprising a PDGF solution disposed in a biocompatible matrix, applying the composition into the site of desired bone fusion, suturing soft tissues over the composition, and permitting cellular migration and infiltration into the composition for subsequent formation of bone.

In some embodiments, an arthrodetic procedure comprises subtalar arthrodesis. In other embodiments, an arthrodetic procedure comprises talonavicular arthrodesis. In another embodiment, an arthrodetic procedure comprises triple arthrodesis. In some embodiments, an arthrodetic procedure comprises a calcaneocuboid arthrodesis. In a further embodiment, an arthrodetic procedure comprises an ankle arthrodesis.

In some embodiments, an arthrodetic procedure comprises a mid-foot fusion (the first, second, third or all 3 medial tarsometatarsal (TMT) joints). In other embodiments, an arthrodetic procedure comprises a naviculocuneiform (NC) joint fusion. In another embodiment, an arthrodetic procedure comprises a first metatarsophalangeal (MP) joint fusion. In a further embodiment, an arthrodetic procedure comprises an interphalangeal joint fusion procedure.

Accordingly, it is an object of the present invention to provide compositions comprising PDGF incorporated in a biocompatible matrix wherein the compositions are useful in facilitating the fusion of bones in arthrodetic procedures.

Another object of the present invention is to provide arthrodetic procedures using a composition comprising PDGF in a biocompatible matrix.

It is another object of the present invention to provide a composition comprising PDGF incorporated in a matrix and a method of using this composition to facilitate bone graft formation in arthrodetic procedures.

Another object of the present invention is to provide compositions comprising PDGF incorporated in a matrix which serve as alternatives to autologous bone grafts in arthrodetic procedures.

A further object of the present invention is to accelerate healing associated with bone fusion in arthrodetic procedures.

These and other embodiments of the present invention are described in greater detail in the description which follows. These and other objects, features, and advantages of the present invention will become apparent after review of the following detailed description of the disclosed embodiments and claims.

DETAILED DESCRIPTION

The present invention provides for the use of compositions of the present invention for use in arthrodetic procedures. The present invention additionally provides for the use of compositions of the present invention in the preparation of an implant material useful for the fusion of bones in a joint. The present invention additionally provides for the use of compositions of the present invention in the preparation of a medicament useful for the fusion of bones in a joint.

The present invention provides compositions and methods for promoting the fusion of bone in arthrodetic procedures, including arthrodetic procedures of the foot and ankle. In one embodiment, a composition for promoting bone fusion in an arthrodetic procedure comprises a solution comprising PDGF and a biocompatible matrix, wherein the solution is disposed or incorporated in the biocompatible matrix. In another embodiment, a composition comprises a PDGF solution disposed in a biocompatible matrix, wherein the biocompatible matrix comprises a bone scaffolding material and a biocompatible binder.

In some embodiments, the PDGF is absorbed by the biocompatible matrix. In other embodiments, the PDGF is adsorbed onto one or more surfaces of the biocompatible matrix. In a further embodiment, the PDGF is absorbed by the biocompatible matrix and adsorbed onto surfaces of the biocompatible matrix.

The present invention also provides a kit comprising a biocompatible matrix in a first package and a solution comprising PDGF in a second package. In some embodiments, the solution comprises a predetermined concentration of PDGF. In some embodiments, the concentration of PDGF is consistent with the values provided herein. The concentration of the PDGF can be predetermined according to the arthrodetic procedure(s) being performed. Moreover, in some embodiments, the biocompatible matrix can be present in the kit in a predetermined amount. The biocompatible matrix may optionally contain a biocompatible binder, or the binder may be provided in a third package in the kit. The amount of biocompatible matrix provided by a kit can be dependent on the arthrodetic procedure(s) being performed. In some embodiments, the second package containing the PDGF solution comprises a syringe. A syringe can facilitate disposition of the PDGF solution in the biocompatible matrix for application at a surgical site, such as a site of bone fusion in an arthrodetic procedure.

Turning now to components that can be included in various embodiments of the present invention, compositions of the present invention comprise a solution comprising PDGF.

PDGF Solutions

In one aspect, a composition for arthrodetic procedures provided by the present invention comprises a solution comprising PDGF and a biocompatible matrix, wherein the solution is disposed or incorporated in the biocompatible matrix. In some embodiments, PDGF is present in the solution in a concentration ranging from about 0.01 mg/ml to about 10 mg/ml, from about 0.05 mg/ml to about 5 mg/ml, or from about 0.1 mg/ml to about 1.0 mg/ml. PDGF may be present in the solution at any concentration within these stated ranges, including the upper limit and lower limit of each range. In other embodiments, PDGF is present in the solution at any one of the following concentrations: about 0.05 mg/ml; about 0.1 mg/ml; about 0.15 mg/ml; about 0.2 mg/ml; about 0.25 mg/ml; about 0.3 mg/ml; about 0.35 mg/ml; about 0.4 mg/ml; about 0.45 mg/ml; about 0.5 mg/ml; about 0.55 mg/ml; about 0.6 mg/ml; about 0.65 mg/ml; about 0.7 mg/ml; about 0.75 mg/ml; about 0.8 mg/ml; about 0.85 mg/ml; about 0.9 mg/ml; about 0.95 mg/ml; or about 1.0 mg/ml. It is to be understood that these concentrations are simply examples of particular embodiments, and that the concentration of PDGF may be within any of the concentration ranges stated above, including the upper limit and lower limit of each range.

Various amounts of PDGF may be used in the compositions of the present invention. Amounts of PDGF that are used, in some embodiments, include amounts in the following ranges: about 1 µg to about 50 mg, about 10 µg to about 25 mg, about 100 µg to about 10 mg, or about 250 µg to about 5 mg.

The concentration of PDGF or other growth factors in embodiments of the present invention can be determined by using an enzyme-linked immunoassay as described in U.S. Pat. Nos. 6,221,625, 5,747,273, and 5,290,708, incorporated herein by reference, or any other assay known in the art for determining PDGF concentration. When provided herein, the molar concentration of PDGF is determined based on the molecular weight (MW) of PDGF dimer (e.g., PDGF-BB; MW about 25 kDa).

In embodiments of the present invention, PDGF comprises PDGF homodimers and heterodimers, including PDGF-AA, PDGF-BB, PDGF-AB, PDGF-CC, PDGF-DD, and mixtures and derivatives thereof. In one embodiment, PDGF comprises PDGF-BB. In another embodiment PDGF comprises a recombinant human (rh) PDGF, such as rhPDGF-BB.

PDGF, in some embodiments, can be obtained from natural sources. In other embodiments, PDGF can be produced by recombinant DNA techniques. In other embodiments, PDGF or fragments thereof may be produced using peptide synthesis techniques known to one of ordinary skill in the art, such as solid phase peptide synthetic. When obtained from natural sources, PDGF can be derived from biological fluids. Biological fluids, according to some embodiments, can comprise any treated or untreated fluid associated with living organisms including blood Biological fluids, in another embodiment, can also comprise blood components including platelet concentrate (PC), apheresed platelets, platelet-rich plasma (PRP), plasma, serum, fresh frozen plasma (FFP), and buffy coat (BC). Biological fluids, in a further embodiment, can comprise platelets separated from plasma and resuspended in a physiological fluid.

When PDGF is produced by recombinant DNA techniques, a DNA sequence encoding a single monomer (e.g., PDGF B-chain or A-chain), in some embodiments, can be inserted into cultured prokaryotic or eukaryotic cells for expression to subsequently produce the homodimer (e.g. PDGF-BB or PDGF-AA). In other embodiments, a PDGF heterodimer can be generated by inserting DNA sequences encoding for both monomeric units of the heterodimer into cultured prokaryotic or eukaryotic cells and allowing the translated monomeric units to be processed by the cells to produce the heterodimer (e.g. PDGF-AB). Commercially available GMP recombinant PDGF-BB can be obtained commercially from Chiron Corporation (Emeryville, Calif.). Research grade rhPDGF-BB can be obtained from multiple sources including R&D Systems, Inc. (Minneapolis, Minn.), BD Biosciences (San Jose, Calif.), and Chemicon, International (Temecula, Calif.).

In embodiments of the present invention, PDGF comprises PDGF fragments. In one embodiment rhPDGF-B comprises the following fragments: amino acid sequences 1-31, 1-32, 33-108, 33-109, and/or 1-108 of the entire B chain. The complete amino acid sequence (1-109) of the B chain of PDGF is provided in FIG. 15 of U.S. Pat. No. 5,516,896. It is to be understood that the rhPDGF compositions of the present invention may comprise a combination of intact rhPDGF-B (1-109) and fragments thereof. Other fragments of PDGF may be employed such as those disclosed in U.S. Pat. No.

5,516,896. In accordance with one embodiment, the rhPDGF-BB comprises at least 65% of intact rhPDGF-B (1-109). In another embodiment, the rhPDGF-BB comprises at least 75%, 80%, 85%, 90%, 95%, or 99% of intact rhPDGF-B (1-109).

In some embodiments of the present invention, PDGF can be purified. Purified PDGF, as used herein, comprises compositions having greater than about 95% by weight PDGF prior to incorporation in solutions of the present invention. The solution may be any pharmaceutically acceptable solution. In other embodiments, the PDGF can be substantially purified. Substantially purified PDGF, as used herein, comprises compositions having about 5% to about 95% by weight PDGF prior to incorporation into solutions of the present invention. In one embodiment, substantially purified PDGF comprises compositions having about 65% to about 95% by weight PDGF prior to incorporation into solutions of the present invention. In other embodiments, substantially purified PDGF comprises compositions having about 70% to about 95%, about 75% to about 95%, about 80% to about 95%, about 85% to about 95%, or about 90% to about 95%, by weight PDGF, prior to incorporation into solutions of the present invention. Purified PDGF and substantially purified PDGF may be incorporated into scaffolds and binders.

In a further embodiment, PDGF can be partially purified. Partially purified PDGF, as used herein, comprises compositions having PDGF in the context of platelet rich plasma (PRP), fresh frozen plasma (FFP), or any other blood product that requires collection and separation to produce PDGF. Embodiments of the present invention contemplate that any of the PDGF isoforms provided herein, including homodimers and heterodimers, can be purified or partially purified. Compositions of the present invention containing PDGF mixtures may contain PDGF isoforms or PDGF fragments in partially purified proportions. Partially purified and purified PDGF, in some embodiments, can be prepared as described in U.S. patent application Ser. No. 11/159,533 (Publication No: 20060084602).

In some embodiments, solutions comprising PDGF are formed by solubilizing PDGF in one or more buffers. Buffers suitable for use in PDGF solutions of the present invention can comprise, but are not limited to, carbonates, phosphates (e.g. phosphate buffered saline), histidine, acetates (e.g. sodium acetate), acidic buffers such as acetic acid and HCl, and organic buffers such as lysine, Tris buffers (e.g. tris(hydroxymethyl)aminoethane), N-2-hydroxyethylpiperazine-N'-2-ethanesulfonic acid (HEPES), and 3-(N-morpholino)propanesulfonic acid (MOPS). Buffers can be selected based on biocompatibility with PDGF and the buffer's ability to impede undesirable protein modification. Buffers can additionally be selected based on compatibility with host tissues. In one embodiment, sodium acetate buffer is used. The buffers can be employed at different molarities, for example, about 0.1 mM to about 100 mM, about 1 mM to about 50 mM, about 5 mM to about 40 mM, about 10 mM to about 30 mM, or about 15 mM to about 25 mM, or any molarity within these ranges. In some embodiments, an acetate buffer is employed at a molarity of about 20 mM.

In another embodiment, solutions comprising PDGF are formed by solubilizing lyophilized PDGF in water, wherein prior to solubilization the PDGF is lyophilized from an appropriate buffer.

Solutions comprising PDGF, according to embodiments of the present invention, can have a pH ranging from about 3.0 to about 8.0. In one embodiment, a solution comprising PDGF has a pH ranging from about 5.0 to about 8.0, from about 5.5 to about 7.0, or from about 5.5 to about 6.5, or any value within these ranges. The pH of solutions comprising PDGF, in some embodiments, can be compatible with the prolonged stability and efficacy of PDGF or any other desired biologically active agent. PDGF may be more stable in an acidic environment. Therefore, in accordance with one embodiment, the present invention comprises an acidic storage formulation of a PDGF solution. In accordance with this embodiment, the PDGF solution preferably has a pH from about 3.0 to about 7.0 or from about 4.0 to about 6.0. The biological activity of PDGF, however, can be optimized in a solution having a neutral pH range. Therefore, in a further embodiment, the present invention comprises a neutral pH formulation of a PDGF solution. In accordance with this embodiment, the PDGF solution has a pH from about 5.0 to about 8.0, from about 5.5 to about 7.0, or from about 5.5 to about 6.5. In accordance with a method of the present invention, an acidic PDGF solution is reformulated to a neutral pH composition, wherein such composition is then used to fuse bones in a joint. In accordance with a preferred embodiment of the present invention, the PDGF utilized in the solutions is rh-PDGF-BB. In a further embodiment, the pH of the PDGF containing solution can be altered to optimize the binding kinetics of PDGF to a biocompatible matrix.

The pH of solutions comprising PDGF, in some embodiments, can be controlled by the buffers recited herein. Various proteins demonstrate different pH ranges in which they are stable. Protein stabilities are primarily reflected by isoelectric points and charges on the proteins. The pH range can affect the conformational structure of a protein and the susceptibility of a protein to proteolytic degradation, hydrolysis, oxidation, and other processes that can result in modification to the structure and/or biological activity of the protein.

In some embodiments, solutions comprising PDGF can further comprise additional components, such as other biologically active agents. In other embodiments, solutions comprising PDGF can further comprise cell culture media, other stabilizing proteins such as albumin, antibacterial agents, protease inhibitors [e.g., ethylenediaminetetraacetic acid (EDTA), ethylene glycol-bis(beta-aminoethylether)-N,N,N', N'-tetraacetic acid (EGTA), aprotinin, ε-aminocaproic acid (EACA), etc.] and/or other growth factors such as fibroblast growth factors (FGFs), epidermal growth factors (EGFs), transforming growth factors (TGFs), keratinocyte growth factors (KGFs), insulin-like growth factors (IGFs), bone morphogenetic proteins (BMPs), or other PDGFs including compositions of PDGF-AA, PDGF-BB, PDGF-AB, PDGF-CC and/or PDGF-DD.

In addition to solutions comprising PDGF, compositions of the present invention also comprise a biocompatible matrix in which to incorporate the PDGF solutions. The compositions may also comprise a biocompatible binder either with or without addition of a biocompatible matrix.

Biocompatible Matrix

In another embodiment of all aspects of the invention, the biocompatible matrix of the implant material is, or additionally includes, one or more bone substituting agents. In another embodiment of all aspects of the invention, the biocompatible matrix of the implant material is, or additionally includes, one or more bone scaffolding material or bone substituting agent and further comprises a biocompatible binder.

Bone Scaffolding Material

A biocompatible matrix, according to embodiments of the present invention, comprises a bone scaffolding material. It is to be understood that the terms bone scaffolding material and bone substituting agent are used interchangeably in this patent application. The bone scaffolding material provides the framework or scaffold for new bone and tissue growth to occur. A bone substituting agent is one that can be used to permanently or temporarily replace bone. Following implantation, the bone substituting agent can be retained by the body or it can be resorbed by the body and replaced with bone. Exemplary bone substituting agents include, e.g., a calcium phosphate (e.g., tricalcium phosphate (e.g., β-TCP), hydroxyapatite, poorly crystalline hydroxyapatite, amorphous calcium phosphate, calcium metaphosphate, dicalcium phosphate dihydrate, heptacalcium phosphate, calcium pyrophosphate dihydrate, calcium pyrophosphate, and octacalcium phosphate), calcium sulfate, mineralized bone, mineralized bone allograft, mineralized deproteinized xenograft, or demineralized bone (e.g., demineralized freeze-dried cortical or cancellous bone)). In an embodiment, the carrier substance is bioresorbable. A bone scaffolding material, in some embodiments, comprises at least one calcium phosphate. In other embodiments, a bone scaffolding material comprises a plurality of calcium phosphates. Calcium phosphates suitable for use as a bone scaffolding material, in embodiments of the present invention, have a calcium to phosphorus atomic ratio ranging from 0.5 to 2.0. In some embodiment, a biocompatible matrix comprises an allograft such as DFDBA or particulate DBM.

Non-limiting examples of calcium phosphates suitable for use as bone scaffolding materials comprise amorphous calcium phosphate, monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), α-tricalcium phosphate, β-TCP, hydroxyapatite (OHAp), poorly crystalline hydroxapatite, tetracalcium phosphate (TTCP), heptacalcium decaphosphate, calcium metaphosphate, calcium pyrophosphate dihydrate, calcium pyrophosphate, carbonated calcium phosphate, or mixtures thereof.

In another embodiment, the bone substituting agent has a porous composition. Porosity is a desirable characteristic as it facilitates cell migration and infiltration into the implant material so that the infiltrating cells can secrete extracellular bone matrix. Porosity also provides access for vascularization. Porosity also provides a high surface area for enhanced resorption and release of active substances, as well as increased cell-matrix interaction. The composition can be provided in a shape suitable for implantation (e.g., a sphere, a cylinder, or a block) or it can be sized and shaped prior to use. In a preferred embodiment, the bone substituting agent is a calcium phosphate (e.g., β-TCP). Porous bone scaffolding materials, according to some embodiments, can comprise pores having diameters ranging from about 1 µm to about 1 mm. In one embodiment, a bone scaffolding material comprises macropores having diameters ranging from about 100 µm to about 1 mm. In another embodiment, a bone scaffolding material comprises mesopores having diameters ranging from about 10 µm to about 100 µm. In a further embodiment, a bone scaffolding material comprises micropores having diameters less than about 10 µm. Embodiments of the present invention contemplate bone scaffolding materials comprising macropores, mesopores, and micropores or any combination thereof.

A porous bone scaffolding material, in one embodiment, has a porosity greater than about 25% or greater than about 40%. In another embodiment, a porous bone scaffolding material has a porosity greater than about 50%, greater than about 60%, greater than about 65%, greater than about 70%, greater than about 80%, or greater than about 85%. In a further embodiment, a porous bone scaffolding material has a porosity greater than about 90%. In some embodiments, a porous bone scaffolding material comprises a porosity that facilitates cell migration into the scaffolding material.

In some embodiments, a bone scaffolding material comprises a plurality of particles. A bone scaffolding material, for example, can comprise a plurality of calcium phosphate particles. Particles of a bone scaffolding material, in some embodiments, can individually demonstrate any of the pore diameters and porosities provided herein for the bone scaffolding. In other embodiments, particles of a bone scaffolding material can form an association to produce a matrix having any of the pore diameters or porosities provided herein for the bone scaffolding material.

Bone scaffolding particles may be mm, µm or submicron (nm) in size. Bone scaffolding particles, in one embodiment, have an average diameter ranging from about 1 µm to about 5 mm. In other embodiments, particles have an average diameter ranging from about 1 mm to about 2 mm, from about 1 mm to about 3 mm, or from about 250 µm to about 750 µm. Bone scaffolding particles, in another embodiment, have an average diameter ranging from about 100 µm to about 300 µm. In a further embodiment, the particles have an average diameter ranging from about 75 µm to about 300 µm. In additional embodiments, bone scaffolding particles have an average diameter less than about 25 µm, less than about 1 µm and, in some cases, less than about 1 mm. In some embodiments, a bone scaffolding particles have an average diameter ranging from about 100 µm to about 5 mm or from about 100 µm to about 3 mm. In other embodiments, bone scaffolding particles have an average diameter ranging from about 250 µm to about 2 mm, from about 250 µm to about 1 mm, from about 200 µm to about 3 mm. Particles may also be in the range of about 1 nm to about 1000 nm, less than about 500 nm or less than about 250 nm.

Bone scaffolding materials, according to some embodiments, can be provided in a shape suitable for implantation (e.g., a sphere, a cylinder, or a block). In other embodiments, bone scaffolding materials are moldable, extrudable, and/or injectable. Moldable, extrudable, and/or injectable bone scaffolding materials can facilitate efficient placement of compositions of the present invention in and around target sites in bone and between bones at sites of desired bone fusion during arthrodetic procedures. In some embodiments, moldable bone scaffolding materials can be applied to sites of bone fusion with a spatula or equivalent device. In some embodiments, bone scaffolding materials are flowable. Flowable bone scaffolding materials, in some embodiments, can be applied to sites of bone fusion through a syringe and needle or cannula. In some embodiments, bone scaffolding materials harden in vivo.

In some embodiments, bone scaffolding materials are bioresorbable. A bone scaffolding material, in one embodiment, can be at least 30%, 40%, 50%, 60%, 70%, 75% or 90% resorbed within one year subsequent to in vivo implantation. In another embodiment, a bone scaffolding material can be resorbed at least 5%, 10%, 20%, 30%, 40%, 50%, 60%, 70%, 75% or 90% within 1, 3, 6, 9, 12, or 18 months of in vivo implantation. Bioresorbability will be dependent on: (1) the nature of the matrix material (i.e., its chemical make up, physical structure and size); (2) the location within the body in which the matrix is placed; (3) the amount of matrix material that is used; (4) the metabolic state of the patient (diabetic/non-diabetic, osteoporotic, smoker, old age, steroid use, etc.); (5) the extent and/or type of injury treated; and (6) the use of other materials in addition to the matrix such as other bone anabolic, catabolic and anti-catabolic factors.

Bone Scaffolding Comprising β-Tricalcium Phosphate

In one embodiment, a bone scaffolding material for use as a biocompatible matrix can comprise β-TCP. β-TCP, according to some embodiments, can comprise a porous structure having multidirectional and interconnected pores of varying diameters. In some embodiments, β-TCP comprises a plurality of pockets and non-interconnected pores of various diameters in addition to the interconnected pores. The porous structure of β-TCP, in one embodiment, comprises macropores having diameters ranging from about 100 μm to about 1 mm, mesopores having diameters ranging from about 10 μm to about 100 μm, and micropores having diameters less than about 10 μm. Macropores and micropores of the β-TCP can facilitate osteoinduction and osteoconduction while macropores, mesopores and micropores can permit fluid communication and nutrient transport to support bone regrowth throughout the β-TCP biocompatible matrix.

In comprising a porous structure, β-TCP, in some embodiments, can have a porosity greater than 25% or greater than about 40%. In other embodiments, β-TCP can have a porosity greater than 50%, greater than about 60%, greater than about 65%, greater than about 70%, greater than about 75%, greater than about 80%, or greater than about 85%. In a further embodiment, β-TCP can have a porosity greater than 90%. In some embodiments, β-TCP can have a porosity that facilitates cell migration into the β-TCP.

In some embodiments, a bone scaffolding material comprises β-TCP particles. β-TCP particles, in some embodiments, can individually demonstrate any of the pore diameters and porosities provided herein for β-TCP. In other embodiments, β-TCP particles of a bone scaffolding material can form an association to produce a matrix having any of the pore diameters or porosities provided herein for the bone scaffolding material. Porosity facilitates cell migration and infiltration into the matrix for subsequent bone formation.

β-TCP particles, in one embodiment, have an average diameter ranging from about 1 μm to about 5 mm. In other embodiments, β-TCP particles have an average diameter ranging from about 1 mm to about 2 mm, from about 1 mm to about 3 mm, from about 250 μm to about 750 μm, from about 250 μm to about 1 mm, from about 250 μm to about 2 mm, or from about 200 μm to about 3 mm. In another embodiment, β-TCP particles have an average diameter ranging from about 100 μm to about 300 μm. In a further embodiment, β-TCP particles have an average diameter ranging from about 75 μm to about 300 μm. In additional embodiments, β-TCP particles have an average diameter less than about 25 μm, average diameter less than about 1 μm, or less than about 1 mm. In some embodiments, β-TCP particles have an average diameter ranging from about 100 μm to about 5 mm or from about 100 μm to about 3 mm.

A biocompatible matrix comprising β-TCP particles, in some embodiments, can be provided in a shape suitable for implantation (e.g., a sphere, a cylinder, or a block). In other embodiments, a β-TCP bone scaffolding material can be moldable, extrudable, and/or injectable thereby facilitating placement of the matrix in and around target sites of desired bone fusion during arthrodetic procedures, such as those in the foot and/or ankle Flowable matrices may be applied through syringes, tubes, or spatulas or equivalent devices. Flowable β-TCP bone scaffolding materials, in some embodiments, can be applied to sites of bone fusion through a syringe and needle or cannula. In some embodiments, β-TCP bone scaffolding materials harden in vivo.

A β-TCP bone scaffolding material, according to some embodiments, is bioresorbable. In one embodiment, a β-TCP bone scaffolding material can be at least 30%, 40%, 50%, 60%, 65%, 70%, 75%, 80%, or 85% resorbed one year subsequent to in vivo implantation. In another embodiment, a β-TCP bone scaffolding material can be greater than 90% resorbed one year subsequent to in vivo implantation.

Bone Scaffolding Material and Biocompatible Binder

In another embodiment, a biocompatible matrix comprises a bone scaffolding material and a biocompatible binder. Bone scaffolding materials in embodiments of a biocompatible matrix further comprising a biocompatible binder are consistent with those provided hereinabove.

Biocompatible binders, according to some embodiments, can comprise materials operable to promote cohesion between combined substances. A biocompatible binder, for example, can promote adhesion between particles of a bone scaffolding material in the formation of a biocompatible matrix. In certain embodiments, the same material may serve as both a scaffolding material and a binder if such material acts to promote cohesion between the combined substances and provides a framework for new bone growth to occur.

Biocompatible binders, in some embodiments, can comprise collagen, polysaccharides, nucleic acids, carbohydrates, proteins, polypeptides, poly(α-hydroxy acids), poly (lactones), poly(amino acids), poly(anhydrides), polyurethanes, poly(orthoesters), poly(anhydride-co-imides), poly(orthocarbonates), poly(α-hydroxy alkanoates), poly(dioxanones), poly(phosphoesters), polylactic acid, poly (L-lactide) (PLLA), poly(D,L-lactide) (PDLLA), polyglycolide (PGA), poly(lactide-co-glycolide (PLGA), poly(L-lactide-co-D,L-lactide), poly(D,L-lactide-co-trimethylene carbonate), polyglycolic acid, polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-polypropylene oxide) block copolymers, poly(ethylene terephthalate)polyamide, and copolymers and mixtures thereof.

Biocompatible binders, in other embodiments, can comprise alginic acid, arabic gum, guar gum, xantham gum, gelatin, chitin, chitosan, chitosan acetate, chitosan lactate, chondroitin sulfate, lecithin, N,O-carboxymethyl chitosan, phosphatidylcholine derivatives, a dextran (e.g., α-cyclodextrin, β-cyclodextrin, γ-cyclodextrin, or sodium dextran sulfate), fibrin glue, lecithin, glycerol, hyaluronic acid, sodium hyaluronate, a cellulose (e.g., methylcellulose, carboxymethylcellulose, hydroxypropyl methylcellulose, or hydroxyethyl cellulose), a glucosamine, a proteoglycan, a starch (e.g., hydroxyethyl starch or starch soluble), lactic acid, a pluronic acid, sodium glycerophosphate, glycogen, a keratin, silk, and derivatives and mixtures thereof.

In some embodiments, a biocompatible binder is water-soluble. A water-soluble binder can dissolve from the biocompatible matrix shortly after its implantation, thereby introducing macroporosity into the biocompatible matrix. Macroporosity, as discussed herein, can increase the osteoconductivity of the implant material by enhancing the access and, consequently, the remodeling activity of the osteoclasts and osteoblasts at the implant site.

In some embodiments, a biocompatible binder can be present in a biocompatible matrix in an amount ranging from about 1 weight percent to about 70 weight percent, about 5 weight percent to about 50 weight percent, about 10 weight percent to about 40 weight percent, about 15 weight percent to about 35 weight percent, or about 15 weight percent to about 25 weight percent of the biocompatible matrix. In a further embodiment, a biocompatible binder can be present in an amount of about 20 weight percent of the biocompatible matrix.

A biocompatible matrix comprising a bone scaffolding material and a biocompatible binder, according to some embodiments, can be flowable, moldable, and/or extrudable. In such embodiments, a biocompatible matrix can be in the form of a paste or putty. A biocompatible matrix in the form of a paste or putty, in one embodiment, can comprise particles of a bone scaffolding material adhered to one another by a biocompatible binder.

A biocompatible matrix in paste or putty form can be molded into the desired implant shape or can be molded to the contours of the implantation site. In one embodiment, a biocompatible matrix in paste or putty form can be injected into an implantation site with a syringe or cannula.

In some embodiments, a biocompatible matrix in paste or putty form does not harden and retains a flowable and moldable form subsequent to implantation. In other embodiments, a paste or putty can harden subsequent to implantation, thereby reducing matrix flowability and moldability.

A biocompatible matrix comprising a bone scaffolding material and a biocompatible binder, in some embodiments, can also be provided in a predetermined shape including a block, sphere, or cylinder or any desired shape, for example a shape defined by a mold or a site of application.

A biocompatible matrix comprising a bone scaffolding material and a biocompatible binder, in some embodiments, is bioresorbable as described above. A biocompatible matrix, in such embodiments, can be resorbed within one year of in vivo implantation. In another embodiment, a biocompatible matrix comprising a bone scaffolding material and a biocompatible binder can be resorbed within 1, 3, 6, or 9 months of in vivo implantation. Bioresorbablity will be dependent on: (1) the nature of the matrix material (i.e., its chemical make up, physical structure and size); (2) the location within the body in which the matrix is placed; (3) the amount of matrix material that is used; (4) the metabolic state of the patient (diabetic/non-diabetic, osteoporotic, smoker, old age, steroid use, etc.); (5) the extent and/or type of injury treated; and (6) the use of other materials in addition to the matrix such as other bone anabolic, catabolic and anti-catabolic factors.

Biocompatible Matrix Comprising β-TCP and Collagen

In some embodiments, a biocompatible matrix can comprise a β-TCP bone scaffolding material and a biocompatible collagen binder. β-TCP bone scaffolding materials suitable for combination with a collagen binder are consistent with those provided hereinabove.

A collagen binder, in some embodiments, can comprise any type of collagen, including Type I, Type II, and Type III collagens. In one embodiment, a collagen binder comprises a mixture of collagens, such as a mixture of Type I and Type II collagen. In other embodiments, a collagen binder is soluble under physiological conditions. Other types of collagen present in bone or musculoskeletal tissues may be employed. Recombinant, synthetic and naturally occurring forms of collagen may be used in the present invention.

A biocompatible matrix, according to some embodiments, can comprise a plurality of β-TCP particles adhered to one another with a collagen binder. β-TCP particles suitable for use with a collagen binder can comprise any of the β-TCP particles described herein. In one embodiment, β-TCP particles suitable for combination with a collagen binder have an average diameter ranging from about 1 μm to about 5 mm. In another embodiment, β-TCP particles suitable for combination with a collagen binder have an average diameter ranging from about 1 μm to about 1 mm, from about 1 mm to about 2 mm, from about 1 mm to about 3 mm, from about 250 μm to about 750 μm, from about 250 μm to about 1 mm, from about 250 μm to about 2 mm, from about 200 μm to about 1 mm, or from about 200 μm to about 3 mm. β-TCP particles, in other embodiments, have an average diameter ranging from about 100 mm to about 300 μm. In a further embodiment, β-TCP particles suitable for combination with a collagen binder have an average diameter ranging from about 75 μm to about 300 μm. In additional embodiments, β-TCP particles suitable for combination with a collagen binder have an average diameter less than about 25 μm and, less than about 1 mm or less than about 1 μm. In some embodiments, β-TCP particles suitable for combination with a collagen binder have an average diameter ranging from about 100 μm to about 5 mm or from about 100 Ξm to about 3 mm.

β-TCP particles, in some embodiments, can be adhered to one another by the collagen binder so as to produce a biocompatible matrix having a porous structure. In some embodiments, a biocompatible matrix comprising β-TCP particles and a collagen binder can comprise pores having diameters ranging from about 1 μm to about 1 mm. A biocompatible matrix comprising β-TCP particles and a collagen binder can comprise macropores having diameters ranging from about 100 μm to about 1 mm, mesopores having diameters ranging from about 10 μm to 100 μm, and micropores having diameters less than about 10 μm.

A biocompatible matrix comprising β-TCP particles and a collagen binder can have a porosity greater than about 25% or greater than 40%. In another embodiment, the biocompatible matrix can have a porosity greater than about 50%, greater than about 60%, greater than about 65%, greater than about 70%, greater than about 80%, or greater than about 85%. In a further embodiment, the biocompatible matrix can have a porosity greater than about 90%. Porosity facilitates cell migration and infiltration into the matrix for subsequent bone formation.

A biocompatible matrix comprising β-TCP particles, in some embodiments, can comprise a collagen binder in an amount ranging from about 1 weight percent to about 70 weight percent, from about 5 weight percent to about 50 weight percent, from about 10 weight percent to about 40 weight percent, from about 15 weight percent to about 35 weight percent, or from about 15 weight percent to about 25 weight percent of the biocompatible matrix. In a further embodiment, a collagen binder can be present in an amount of about 20 weight percent of the biocompatible matrix.

A biocompatible matrix comprising β-TCP particles and a collagen binder, according to some embodiments, can be flowable, moldable, and/or extrudable. In such embodiments, the biocompatible matrix can be in the form of a paste or putty. A paste or putty can be molded into the desired implant shape or can be molded to the contours of the implantation site. In one embodiment, a biocompatible matrix in paste or putty form comprising β-TCP particles and a collagen binder can be injected into an implantation site with a syringe or cannula.

In some embodiments, a biocompatible matrix in paste or putty form comprising β-TCP particles and a collagen binder can retain a flowable and moldable form when implanted. In other embodiments, the paste or putty can harden subsequent to implantation, thereby reducing matrix flowability and moldability.

A biocompatible matrix comprising β-TCP particles and a collagen binder, in some embodiments, can be provided in a predetermined shape such as a block, sphere, or cylinder.

A biocompatible matrix comprising β-TCP particles and a collagen binder can be resorbable. In one embodiment, a biocompatible matrix comprising β-TCP particles and a collagen binder can be at least 30%, 40%, 50%, 60%, 70%, 75%, or 90% resorbed one year subsequent to in vivo implantation. In another embodiment, this matrix can be resorbed at least 5%, 10%, 20%, 30%, 40%, 50%, 60%, 70%, 75% or 90% within 1, 3, 6, 9, 12, or 18 months subsequent to in vivo implantation.

A solution comprising PDGF can be disposed in a biocompatible matrix to produce a composition for promoting bone fusion in arthrodetic procedures according to embodiments of the present invention.

Incorporating PDGF Solution in a Biocompatible Matrix

The present invention provides methods for producing compositions for use in arthrodetic procedures. In one embodiment, a method for producing a composition for promoting the fusion of bone comprises providing a solution comprising PDGF, providing a biocompatible matrix, and incorporating the solution in the biocompatible matrix. PDGF solutions and biocompatible matrices suitable for combination are consistent with those described hereinabove.

In one embodiment, a PDGF solution can be incorporated in a biocompatible matrix by soaking the biocompatible matrix in the PDGF solution. A PDGF solution, in another embodiment, can be incorporated in a biocompatible matrix by injecting the biocompatible matrix with the PDGF solution. In some embodiments, injecting a PDGF solution can comprise incorporating the PDGF solution in a syringe and expelling the PDGF solution into the biocompatible matrix to saturate the biocompatible matrix.

The biocompatible matrix, according to some embodiments, can be in a predetermined shape, such as a brick or cylinder, prior to receiving a PDGF solution. Subsequent to receiving a PDGF solution, the biocompatible matrix can have a paste or putty form that is flowable, extrudable, and/or injectable. In other embodiments, the biocompatible matrix can already demonstrate a flowable paste or putty form prior to receiving a solution comprising PDGF.

Compositions Further Comprising Biologically Active Agents

The compositions described herein for promoting and/or facilitating bone fusion in arthrodetic procedures, according to some embodiments, can further comprise one or more biologically active agents in addition to PDGF. Biologically active agents that can be incorporated into compositions of the present invention in addition to PDGF can comprise organic molecules, inorganic materials, proteins, peptides, nucleic acids (e.g., genes, gene fragments, small insert ribonucleic acids [si-RNAs], gene regulatory sequences, nuclear transcriptional factors, and antisense molecules), nucleoproteins, polysaccharides (e.g., heparin), glycoproteins, and lipoproteins. Non-limiting examples of biologically active compounds that can be incorporated into compositions of the present invention, including, e.g., anti-cancer agents, antibiotics, analgesics, anti-inflammatory agents, immunosuppressants, enzyme inhibitors, antihistamines, hormones, muscle relaxants, prostaglandins, trophic factors, osteoinductive proteins, growth factors, and vaccines, are disclosed in U.S. patent application Ser. No. 11/159,533 (Publication No: 20060084602). In some embodiments, biologically active compounds that can be incorporated into compositions of the present invention include osteoinductive factors such as insulin-like growth factors, fibroblast growth factors, or other PDGFs. In accordance with other embodiments, biologically active compounds that can be incorporated into compositions of the present invention preferably include osteoinductive and osteostimulatory factors such as bone morphogenetic proteins (BMPs), BMP mimetics, calcitonin, calcitonin mimetics, statins, statin derivatives, or parathyroid hormone. Preferred factors also include protease inhibitors, as well as osteoporotic treatments that decrease bone resorption including bisphosphonates, and antibodies to receptor activator of NF-kB ligand (RANK) ligand.

Standard protocols and regimens for delivery of additional biologically active agents are known in the art. Additional biologically active agents can be introduced into compositions of the present invention in amounts that allow delivery of an appropriate dosage of the agent to the implant site. In most cases, dosages are determined using guidelines known to practitioners and applicable to the particular agent in question. The amount of an additional biologically active agent to be included in a composition of the present invention can depend on such variables as the type and extent of the condition, the overall health status of the particular patient, the formulation of the biologically active agent, release kinetics, and the bioresorbability of the biocompatible matrix. Standard clinical trials may be used to optimize the dose and dosing frequency for any particular additional biologically active agent.

A composition for promoting bone fusion in arthrodetic procedures, according to some embodiments, can further comprise the addition of other bone grafting materials with PDGF including autologous bone marrow, autologous platelet extracts, and synthetic bone matrix materials.

Methods of Performing Arthrodetic Procedures

The present invention also provides methods of performing arthrodetic procedures. In one embodiment, a method of performing an arthrodetic procedure comprises providing a composition comprising a PDGF solution incorporated in a biocompatible matrix and applying the composition to a site of desired bone fusion in a joint. In some embodiments, a method of performing an arthrodetic procedure comprises applying the composition to a site of desired bone fusion in a plurality of joints. A composition comprising a PDGF solution incorporated in a biocompatible matrix, for example, can be packed into a site of desired bone fusion in a joint. In some embodiments, the composition can be packed such that the composition is in contact with the entire surface area of the bones to be fused in the joint. The composition may additionally be applied to the vicinity of the bone fusion site to further strengthen the fused joint.

Bones in any joint may be fused using the compositions and methods of the present invention. Such joints include, but are not limited to joints of the foot, toes, ankle, knee, hip, spine, rib, sternum, clavicle, joint, shoulder, scapula, elbow, wrist, hand, fingers, jaw and skull.

In some embodiments, a method of performing an arthrodetic procedure further comprises aligning the joint and inserting at least one fixation device, such as a screw, into at least one bone of the joint. In some embodiments, a plurality of screws are inserted into at least one bone of the joint.

In another embodiment, a method of the present invention comprises accelerating bony union in an arthrodetic procedure wherein accelerating bony union comprises providing a composition comprising a PDGF solution disposed in a biocompatible matrix and applying the composition to at least one site of bone fusion in a joint.

It is to be understood that the present invention may apply to any desired site for arthrodesis in the appendicular or spinal skeleton.

In one embodiment of the present invention, arthrodetic procedures comprise arthrodesis of the foot and ankle including subtalar arthrodesis, talonavicular arthrodesis, triple arthrodesis, and ankle arthrodesis. Example 3 describes a study designed to demonstrate the efficacy of compositions and methods of the present invention for promoting bone fusion in arthrodetic procedures of the foot and ankle.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

Preparation of a Composition Comprising a Solution of PDGF and a Biocompatible Matrix A composition comprising a solution of PDGF and a biocompatible matrix of β-TCP was prepared according to the following procedure. The β-TCP comprised β-TCP particles having an average diameter ranging from about 1000 µm to about 2000 µm.

A solution comprising rhPDGF-BB was obtained. rhPDGF-BB is commercially available from Chiron Corporation at a stock concentration of 10 mg/ml (i.e., Lot #QA2217) in a sodium acetate buffer. The rhPDGF-BB is produced in a yeast expression system by Chiron Corporation and is derived from the same production facility as the rhPDGF-BB that is utilized in the products REGRANEX, (Johnson & Johnson) and GEM 21S (BioMimetic Therapeutics) which has been approved for human use by the United States Food and Drug Administration. This rhPDGF-BB is also approved for human use in the European Union and Canada. The rhPDGF-BB solution was diluted to 0.3 mg/ml in the acetate buffer. The rhPDGF-BB solution can be diluted to any desired concentration according to embodiments of the present invention, including 1.0 mg/ml.

A ratio of about 3 ml of rhPDGF-BB solution to about 1 g dry weight of the β-TCP biocompatible matrix was used to produce the composition. The rhPDGF-BB solution was expelled on the β-TCP particles of the biocompatible matrix with a syringe, and the resulting composition was blended and molded in preparation for application at a site of bone fusion in a joint.

EXAMPLE 2

Preparation of a Composition Comprising a Solution of PDGF, a Biocompatible Matrix and a Biocompatible Binder A composition comprising a solution of PDGF and a biocompatible matrix containing a biocompatible binder, collagen, was prepared according to the following procedure.

A pre-weighed block of biocompatible matrix comprising β-TCP and collagen was obtained. The β-TCP comprised β-TCP particles having an average diameter ranging from about 100 µm to about 300 µm. The β-TCP particles were formulated with approximately 20 weight percent soluble bovine collagen binder. A β-TCP/collagen matrix can be commercially obtained from Kensey Nash (Exton, Pa.).

A solution comprising rhPDGF-BB was obtained. rhPDGF-BB is commercially available from Chiron Corporation at a stock concentration of 10 mg/ml (i.e., Lot #QA2217) in a sodium acetate buffer. The rhPDGF-BB is produced in a yeast expression system by Chiron Corporation and is derived from the same production facility as the rhPDGF-BB that is utilized in the products REGRANEX, (Johnson & Johnson) and GEM 21S (BioMimetic Therapeutics) which has been approved for human use by the United States Food and Drug Administration. This rhPDGF-BB is also approved for human use in the European Union and Canada. The rhPDGF-BB solution was diluted to 0.3 mg/ml in the acetate buffer. The rhPDGF-BB solution can be diluted to any desired concentration according to embodiments of the present invention, including 1.0 mg/ml.

A ratio of about 3 ml of rhPDGF-BB solution to about 1 g dry weight of the β-TCP/collagen matrix was used to produce the composition. The rhPDGF-BB solution was expelled on the β TCP/collagen matrix with a syringe, and the resulting composition was blended and molded in preparation for application at a site of bone fusion in a joint.

EXAMPLE 3

Method of Performing Arthrodesis of the Foot and/or Ankle

Experimental Design and Overview

The purpose of this prospective, randomized, controlled, multi-center feasibility clinical trial was to evaluate the safety and effectiveness of a composition comprising a PDGF solution disposed in a β-TCP matrix compared to autologous bone graft (ABG) in foot/ankle arthrodetic procedures. The clinical significance of comparing a composition of the present invention to autograft provides for a predictable synthetic alternative to autograft, thus eliminating the morbidity and increased surgical time associated with an additional procedure for harvesting autogenous bone graft, which is only available in limited quantities. Additionally, an adjunctive recombinant growth factor eliminates additional procedures associated with harvesting and preparing bone marrow aspirate or autologous platelet concentrates and increases predictability by eliminating concentration variability associated with such systems. Comparisons were made between the control group (Group I: ABG) and compositions comprising a PDGF solution disposed in a β-TCP matrix (Group II: β-TCP-PDGF, as prepared according to Example 1).

The study enrolled 20 patients presenting with a defect requiring bone fusion in the foot and/or ankle. The fusion space was adequately reduced and stabilized with rigid fixation intra-operatively in order to meet final study eligibility. Subjects were randomized. A subject was not enrolled in the study if the surgeon determined on the day of surgery that the bone defect does not meet enrollment criteria or the fusion site cannot be adequately reduced and stabilized according to the protocol.

The treatment groups were: Group I: Standard Rigid Fixation+ABG; and, Group II: Standard Rigid Fixation+β-TCP, with sodium acetate buffer containing 0.3 mg/ml rhPDGF-BB. Subjects in each group were immobilized according to the standard operative and post-operative protocols.

The primary endpoint, mean time to radiographic union (defined as osseous bridging across subchondral surfaces of at least 3 out of 4 bony aspects) was determined based upon plain film radiographs. Computer tomographic (CT) scans provided precise information on union and were taken at periodic intervals as supplemental and confirmatory documentation of healing. Union was determined by independent radiologist(s) assessment based upon the above noted and generally accepted criteria. Clinical and functional assessments consisted of range of motion, time to full weight-bearing (FWB), pain, and patient quality of life/outcomes scores. Also, the length of surgical procedure (i.e. start of first incision to time of closure) was recorded. The schedule for follow-up was followed according to Table 1.

TABLE 1

Study timeline summary

| Visit 1 Screening Visit ↓ | Visit 2 Surgical Visit ↓ | Visit 3 Post Tx Follow Up | Visit 4 Post Tx Follow Up | Visit 5 Post Tx Follow Up | Visit 6 Post Tx Follow Up | Visit 7 Post Tx Follow Up | Visit 8 Post Tx Follow Up | Visit 9 Post Tx Follow Up | Visit 10 Post Tx Follow Up | Visit 11 Post Tx Follow Up |
|---|---|---|---|---|---|---|---|---|---|---|
| Within 21 Days of Surgical Visit | Within 21 Days of Screening | ↓ | ↓ | ↓ | ↓ | ↓ | ↓ | ↓ | ↓ | ↓ |
|  | Day 0 | Day 7-14 | Week 4 ± 7 days | Week 6 ± 7 days | Week 8 ± 7 days | Week 10 ± 7 days | Week 12 ± 7 days | Week 16 ± 14 days | Week 24 ± 14 days | Week 36 ± 14 days |

The primary endpoint was the time to radiographic healing (union) as assessed by plain X-ray films and CT scans. Moreover, secondary radiographic endpoints for evaluating healing in an arthrodetic procedure included callus formation, overall assessment of osseous bridging (CT scans; weeks 6, 12, and 16 only), presence of abnormal bone formation (e.g. heterotopic bone formation, exotosis, hyperplasia), evidence of bone resorption, assessment of β-TCP resoprtion, and hardware complications such as loosening of screws.

In addition to radiographic endpoints, healing in an arthrodetic procedure can be assessed by a variety of clinical and functional endpoints including 24-week union rate, time to full weight bearing, edema/swelling, pain at the surgical site, presence of warmth at the surgical site, evidence of infection and/or ulceration, operative time, incidence of complications or adverse events, and quality of life considerations.

Surgical Protocol

The procedure was performed under either local or general anesthesia, according to co-morbidities and at the discretion of the investigator. Surgical technique was identical in both treatment groups except that Group II had application of the rhPDGF/β-TCP particulate matrix to the site of fusion at the time of rigid fixation, and Group I had ABG applied to the site of fusion at the time of rigid fixation of the fusion site, as specified by the randomization schedule. ABG was harvested either locally or from the iliac crest, as determined by the investigator. In the event a patient was admitted to the hospital after surgery, it would be for reasons separate from the study parameters (e.g., pain control, perioperative complication, medical monitoring, etc.). Any event requiring hospitalization or prolonged hospitalization that was not intended as part of the pre-operative plan was recorded in the case report form and reported to the sponsor.

Operatively, the patient was placed supine with a tourniquet around the thigh. Perioperative prophylactic antibiotics were administered before surgical incision. After routine preparation and draping, standard surgical exposures were employed to gain access to each fusion site. The open surgical approaches employed in this study represent standard medial, lateral, and/or anterior exposures designed to minimize the chance of sensory impairment or neurovascular injury at the time of surgery. The appropriate soft tissues were released as necessary according to standard techniques. This may include tendon release of, for example, the gastrocnemius or Achilles tendon, in the event soft tissue balancing was required to enact more precise anatomic reduction of deformity. The entirety of any involved joint was exposed and denuded to subchondral bone, and the cortices were perforated to augment the subsequent fusion.

The opposing surfaces of the joints to be fused were prepared in standard fashion with the use of small osteotomes, curettes, drilling, a burr, and/or a saw, depending upon the severity of the deformity, the quality of the bone, and the amount of remaining cartilage. Appropriate soft tissues were released as necessary according to standard techniques.

The appropriate joints were subsequently placed in proper alignment and were fused with large fragment screws (3.5 to 7.3 mm, depending upon the size of the patient's foot) to ensure rigid, compressive fixation. The fixation was rigid in order to ensure that the final reduction was maintained during the healing process. No more than four screws were used to ensure rigid fixation. The type of fixation was recorded on the Case Report Form.

A composition of the present invention comprising a PDGF solution disposed in a β-TCP matrix was prepared or ABG was harvested, locally or from the iliac crest, based upon the randomization schedule. Subjects consented to harvesting of local or iliac crest bone graft prior to the surgical procedure, as the subject was blinded to the randomization assignment. For subjects randomized to receive ABG, the harvest site and amount of bone graft was documented on the case report form. Autograft was harvested according to standard bone grafting procedures. The graft material (β-TCP-PDGF or ABG) was packed into the fusion site at the time of fixation such that the graft material was in contact with the entire surface area of the joint to be fused. Approximately 3 to 6 cc of graft material was required for the fusion of each joint. As a general guideline, it was expected that 9 cc would be used for the triple arthrodesis, 6 cc for the subtalar and ankle fusions, and 3 cc for the talonavicular and calcaneocuboid fusions. Those patients randomized to receive ABG undergo an additional surgical incision separate from those required to perform the fusion procedure in the foot/ankle, and those randomized to receive β-TCP-PDGF did not require such additional surgery. The inherent risks and potential benefits of these different approaches were outlined in the surgical consent form.

For multiple fusion procedures, such as triple arthrodesis or talonavicular fusion, an individual (single) joint was defined by the investigator according to defined parameters as the primary fusion site for the purpose of the statistical analysis. Healing/union was assessed collectively for all joints involved as a unit. All involved joint fusions were treated according to the randomization schedule.

Following final fixation of the deformity, additional graft material was placed around the fusion site to maximize graft exposure in order to facilitate osseointegration into the fusion space. Care was taken to ensure that graft material was contained within the fusion space. Once the β-TCP-PDGF or ABG was added in its entirety to the construct, careful layered periosteal and overlying soft tissue closure was performed to enclose and contain this graft and minimize any risk of washout or subperiosteal resorption, exostosis, and ulceration at the surgical site.

began formal physical therapy to help with their progressive weight-bearing (e.g. gait training, edema control, range of motion of unfused joints, scar mobilization). At 12 weeks, the patients were taken out of their cast and placed into a regular walking shoe with the use of an ankle/hindfoot brace for transitional immobilization. The time of radiographic healing (as assessed by the investigator) and release to full weight-bearing was documented by the investigator. The independent radiologist(s) performed a separate and independent assessment of healing. The frequency and nature of radiographic and functional assessments were provided in Table 2.

TABLE 2

Frequency of Radiographic and Functional Assessments

|  |  | Radiographic Parameters | | | Functional Assessments | | | |
|---|---|---|---|---|---|---|---|---|
|  | Event | Quantitative Radiograph Parameters | Semi-Quantitative Radiograph Parameters | Verify Reduction | Range of Motion | Clinical Eval. | Pain | QOL |
| Periop. Management | Prior to Treatment | X | X |  |  | X |  | X |
|  | After Stabilization |  |  | X |  |  |  |  |
|  | During Implementation |  |  | X |  |  |  |  |
|  | Post Reduction/Implantation Prior to Fixation |  |  | X |  |  |  |  |
|  | Immediately Post-Fixation | X | X |  |  | X | X |  |
| Management of Injured Area | Day 7-14 | X | X |  |  | X | X |  |
|  | Week 4 | X | X |  |  |  | X |  |
|  | Week 6 | X | X |  | X | X | X | X |
|  | Week 8 | X | X |  |  | X** | X |  |
|  | Week 10 | X | X |  |  | X** | X |  |
|  | Week 12 | X* | X |  | X | X | X | X |
|  | Week 16 | X* | X |  |  |  | X |  |
|  | Week 24 | X | X |  | X | X | X | X |
|  | Week 36 | X | X |  | X | X | X | X |

*Confirmatory CT scan taken at Weeks 6, 12 and 16 (if union is not achieved by Week 12).
**Clinical evaluations at Wk 8 and 10 are not required if clinical healing was established at Week 6.
Pain to be assessed at the time of hospital discharge, in addition to the noted study visits.

The tourniquet was subsequently deflated, hemostasis carefully maintained, and finally the remainder of the wounds were closed in layers. An ankle block using 0.5% marcaine and 1% lidocaine was administered thereafter to aid in post-operative pain control, and the patient was then placed in a sterile compressive dressing and posterior splint in neutral alignment, awakened from anesthesia, and thereafter discharged to the recovery room.

Follow-Up Evaluation

Subjects were seen for post-operative evaluations at days 7-14 and weeks 4, 6, 8, 10, 12 (+/−7 days), 16, 24, and 36 (+/−14 days) post surgery (Tx), as provided in Table 1. Routine evaluations and procedures were performed during the follow-up period. Post-operatively, the foot or ankle was immobilized in a posterior splint for one to two weeks, at which point each was seen for a first post-operative visit for suture removal and application of a short leg cast (SLC). Following the first two weeks in a splint, all patients were placed in a short leg cast which was serially changed as necessary for proper fitting and integrity over the course of their ensuing patient follow-up visits for the subsequent 10 weeks. Any deviations from protocol were recorded.

Patients remained non weight-bearing for the first 6 weeks post-operatively, after which progressive, partial weight-bearing (PWB) began. At 6 weeks post-operatively, patients Results Assessment of computerized tomography (CT) scans of joint fusion sites by an independent reviewer blinded to the treatment groups indicated that at 6 weeks 39% of the patients in Group II receiving the composition comprising rhPDGF-BB incorporated in a β-TCP matrix exhibited osseous bridging of greater than 50% in comparison to 34% of autograft patients. Moreover, at 12 weeks, 63% of patients in Group II exhibited osseous bridging of greater than 50% at joint fusion sites in comparison with 50% of the patients in Group I.

In the clinical evaluations (physician scored AOFAS evaluation) at the six week time point, patients of Group II displayed an average score of 56.2 while patients of Group I displayed an average score of 52.3. The higher score of Group II indicated improved function of the treated joint areas. Additionally, in the patient scored pain assessment (VAS assessment), patients of Group II demonstrated an average score of 16.3, and patients of Group I demonstrated an average score of 26.1 at six weeks. The lower score of patients of Group II indicated a more favorable outcome of the arthrodetic procedure in relation to patient quality of life. Furthermore, patients of Group II receiving the β-TCP+rhPDGF-BB composition did not display any ectopic bone formation or adverse effects on surrounding or distant soft tissues.

EXAMPLE 4

Partial Arthrodesis of the Carpus in Dogs

Experimental Design and Overview

This study evaluated the safety and effectiveness of a composition comprising a solution comprising 0.3 mg/ml PDGF disposed in a β-TCP matrix with or without a collagen binder compared to autologous bone graft in partial arthrodesis of the carpus in dogs. The clinical significance of comparing a composition of the present invention to autograft provides for a predictable synthetic alternative to autograft, thus eliminating the morbidity and increased surgical time associated with an additional procedure for harvesting autogenous bone graft which is only available in limited quantities.

The study enrolled 30 dogs which underwent partial arthrodesis of the carpus. The treatment groups were:
Group I: Autograft (10 dogs)
 1. Autograft+rhPDGF-BB (Side A)
 2. Autograft only (Side B)
Group II: Particulate β-tricalcium phosphate (β-TCP) (10 dogs)
 1. β-TCP+rhPDGF-BB (Side A)
 2. β-TCP only (side B)
Particle sizes of the β-TCP ranged from about 250 μm to about 1 mm The composition was made in a manner similar to that outlined in Example 1.
Group III: β-tricalcium phosphate and collagen binder (β-TCP/collagen) (10 dogs)
 1. β-TCP/collagen+rhPDGF-BB (Side A)
 2. β-TCP/collagen only (side B)
Particle sizes of the β-TCP ranged from about 100 μm to about 300 μm, and the β-TCP/collagen material comprised 20 weight percent Type I collagen.

Animals

Thirty (30) dogs were acquired from Louisiana State University (LSU) Veterinary School of Medicine and delivered to the University of Iowa Office of Animal Resources (OAR). Each animal received a thorough examination and all health records were transferred to the OAR. All dogs were in good health and underwent a 14 day quarantine period prior to study initiation.

Surgical Protocol

Each animal underwent bilateral surgeries with one leg treated with the autograft, β-TCP, or β-TCP/collagen alone and the opposite side treated with the autograft+rh-PDGF-BB, β-TCP+rh-PDGF-BB, or β-TCP/collagen+rh-PDGF-BB. The side for each treatment was randomized for each animal.

Food and water were withheld from the animals 18 hours prior to surgery. Each animal was brought to the operating room (OR) and Thiopental (20-25 mg/kg IV) was given slowly in the jugular vein until the animal was sedated. A 9 mm intubation tube was inserted for inhalation anesthesia (Isoflurane was delivered in $O_2$ at a rate of 2% and was utilized throughout the procedure). An 18 g catheter was inserted in the femoral vein and lactated ringers solution was administered at a rate of 10 ml/kg/hr. Cefazolin (20 mg/kg IV) was also administered. The animal's forelimbs were clipped of all hair and, if the animal was in the autograft group, a 10×10 inch area above the dog's iliac crest was shaved of all hair.

The animal was placed on the operating room table in the prone position, and both forelimbs and hips were surgically prepped with povidone solution. The animal was then draped with surgical drapes.

Autograft Harvest

A 5 cm incision was made over both hips of the animal, and the fascia was incised down to the crest and dissected with a freer. Rongeurs were used to obtain 1.5 cc of corticocancellous autograft from both iliac crests. The fascia was closed with 2.0 Vicryl in a running stitch. The skin was closed in the same routine manner.

Forelimbs

A 5 cm midline dorsal incision was made through the skin just below the cephalic and accessory cephalic veins and extended distally for 5 cm. The deep antebrachial fascia was incised midway between the extensor carpi radialis tendon and the common digital extensor and retracted with a self retaining retractor. A round 2 mm high speed burr was used to denude the joint surfaces of the distal radial carpal, proximal and distal surfaces of the $3^{rd}$ carpal and the proximal surface of the $3^{rd}$ metacarpal. The joint was irrigated with 10 cc of normal saline. Approximately 1 cc of graft material was placed above and below the $3^{rd}$ carpal bone in the joint space.

A 2-T-3 T-plate from Synthes Ltd. of West Chester, Pa. was placed over the joint and a 2 mm drill bit was used to drill two holes in the radial carpal bone as distally as possible to ensure normal movement of the antebrachiocarpal joint. Two 2.7 mm self tapping screws, each 18 mm in length, were placed in the radial carpal to secure the plate. Additional holes were drilled through the $3^{rd}$ metacarpal and $3^{rd}$ carpal bone. Two 2.7 mm self tapping screws were placed in the metacarpal and one in the carpal. The deep and superficial fascial layers were closed with a running stitch of VICRYL® from Johnson and Johnson. The skin was closed in the same routine manner.

The dogs' limbs were cleaned of all dried blood and povidone solution and wrapped in 2 inch soft roll and 2 inch stockinet. Each limb was then wrapped with 3 layers of 2 inch fiberglass casting tape for immobilization. Casts were worn for at least 8 weeks.

Following the surgical procedure, the animal was placed in a recovery pen. Two Fentanyl patches, one 50 μg/hr and one 25 μg/hr were placed on the dogs neck. Flunixin (1 mg/kg) was given subcutaneously. The animal was allowed to wake up and bear weight on the forelimbs. Each animal was evaluated for signs of pain, infection, and eating habits. Appropriate analgesics were administered throughout the study in accordance with IACUC approval. Casts were changed at least once a week. 21 of the 30 dogs were humanely sacrificed at 5 weeks post operatively. The remaining dogs were humanely sacrificed at 12 weeks post operatively.

Evaluation

Radiography

Standard anteroposterior (AP) x-rays were taken at weekly intervals of each animal to assess fixation and to assess new bone formation and fusion of bones bridging the treated joints.

Calcified Histology

Specimen limbs from each group were immersed in 10% formalin for one week, rinsed in water for 24 hours, and subsequently immersed in 70% ethanol. Dehydration was accomplished with an ascending series of alcohols starting from 80% and progressing serially to 90%, 95%, and 100%. Alcohol was cleared with 100% acetone. Each specimen was embedded in Spurrs plastic for calcified histology.

Serial anterior-posterior sections were ground with 1000, 1200, and 2000 grit grinding discs, polished with 2400 grit polishing paper, and stained with hematoxylin and eosin. A board certified veterinary patholigist examined the histological responses of Groups I, II, and III. Bone fusion at treated joints measured as a function of trabecular bone formation across the joint.

Clinical Assessment—Palpation

Palpation at 5 and 12 weeks was used to qualitatively assess joint fusion. One examiner independently determined the existence of joint fusion across all three treatment Groups. The examiner was blinded to the treatment Groups.

Soft tissues were removed from the specimens, and each joint was palpated. The radial carpal and $3^{rd}$ carpal were held, and the bones were stressed to determine the existence of any movement (e.g. fusion across the joint). The same procedure was used for the $3^{rd}$ carpal and $3^{rd}$ metacarpal joint. Results were recorded as "fused" or "not fused."

Results

Thirty (30) dogs entered the study with 28 of the 30 progressing to the terminal stage. Two animals were prospectively omitted. While radiographs were taken weekly as provided herein, visualization of the joint space was not possible until the T-plate was removed. T-plate removal was conducted following humane sacrifice of the animals. As a result, the data presented herein corresponds to post-sacrifice radiographs. The radiographic results detailing osseous bridging are summarized in Tables 3 and 4.

TABLE 3

Five Week Radiographic Osseous Bridging

| Group/Composition | Radial Carpal/$3^{rd}$ Carpal (Percent of Joints Having Osseous Bridging) | $3^{rd}$ Carpal/$3^{rd}$ Metacarpal (Percent of Joints Having Osseous Bridging) |
| --- | --- | --- |
| I. Autograft only | 33 | 67 |
| I. Autograft + rhPDGF-BB | 33 | 100 |
| II. β-TCP only | 29 | 57 |
| II. β-TCP + rhPDGF-BB | 43 | 29 |
| III. β-TCP/collagen | 50 | 83 |
| III. β-TCP/collagen + rhPDGF-BB | 50 | 83 |

TABLE 4

Twelve Week Radiographic Osseous Bridging

| Group/Composition | Radial Carpal/$3^{rd}$ Carpal (Percent of Joints Having Fusion) | $3^{rd}$ Carpal/$3^{rd}$ Metacarpal (Percent of Joints Having Fusion) |
| --- | --- | --- |
| I. Autograft only | 66 | 33 |
| I. Autograft + rhPDGF-BB | 100 | 100 |
| II. β-TCP only | 66 | 66 |
| II. β-TCP + rhPDGF-BB | 66 | 38 |
| III. β-TCP/collagen | 66 | 66 |
| III. β-TCP/collagen + rhPDGF-BB | 100 | 100 |

The results of the palpation assessments are present in Tables 5 and 6.

TABLE 5

Five Week Palpation Osseous Bridging Assessment

| Group/Composition | Radial Carpal/$3^{rd}$ Carpal (Percent of Joints Having Osseous Bridging) | $3^{rd}$ Carpal/$3^{rd}$ Metacarpal (Percent of Joints Having Osseous Bridging) |
| --- | --- | --- |
| I. Autograft only | 50 | 17 |
| I. Autograft + rhPDGF-BB | 67 | 33 |
| II. β-TCP only | 14 | 43 |
| II. β-TCP + rhPDGF-BB | 57 | 43 |
| III. β-TCP/collagen | 50 | 33 |
| III. β-TCP/collagen + rhPDGF-BB | 50 | 67 |

TABLE 6

Twelve Week Palpation Osseous Bridging Assessment

| Group/Composition | Radial Carpal/$3^{rd}$ Carpal (Percent of Joints Having Osseous Bridging) | $3^{rd}$ Carpal/$3^{rd}$ Metacarpal (Percent of Joints Having Osseous Bridging) |
| --- | --- | --- |
| I. Autograft only | 66 | 66 |
| I. Autograft + rhPDGF-BB | 100 | 100 |
| II. β-TCP only | 66 | 66 |
| II. β-TCP + rhPDGF-BB | 66 | 66 |

TABLE 6-continued

Twelve Week Palpation Osseous Bridging Assessment

| Group/Composition | Radial Carpal/3rd Carpal (Percent of Joints Having Osseous Bridging) | 3rd Carpal/3rd Metacarpal (Percent of Joints Having Osseous Bridging) |
|---|---|---|
| III. β-TCP/collagen | 66 | 66 |
| III. β-TCP/collagen + rhPDGF-BB | 100 | 100 |

As demonstrated by the foregoing data, joints treated with compositions comprising rhPDGF-BB displayed enhanced osseous bridging and fusion. Moreover, β-TCP compositions comprising rhPDGF-BB demonstrated osseous bridging and joint fusion results comparable to autograft compositions, thereby precluding the necessity to harvest autograft for arthrodetic procedures. Eliminating autograft harvesting from arthrodetic procedures reduces patient pain and discomfort while facilitating the joint fusion process.

Moreover, the histological results of the present study confirmed normal bone formation processes with no ectopic bone formation or adverse effects on surrounding or distant soft tissues.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

We claim:

1. A method of performing an arthrodetic surgical procedure on a patient comprising:
    a step of surgically accessing a site of desired bone fusion of a joint, and
    a step of applying to the site of desired bone fusion a composition consisting of a platelet derived growth factor (PDGF) solution and a biocompatible matrix, wherein the solution is disposed in the biocompatible matrix,
    wherein the biocompatible matrix consists of a bone scaffolding material or a bone scaffolding material and collagen, wherein the bone scaffolding material consists of a porous calcium phosphate,
    wherein the calcium phosphate consists of particles having an average diameter from about 100 microns to about 5000 microns,
    wherein the calcium phosphate comprises interconnected pores,
    wherein the PDGF solution consists of PDGF at a concentration of about 0.01 to about 10.0 mg/ml in a buffer; and
    wherein the method promotes fusion of bones of the joint.

2. The method of claim 1, wherein the biocompatible matrix consists of the bone scaffolding material.

3. The method of claim 2, wherein the PDGF concentration is about 0.1 to about 1.0 mg/ml.

4. The method of claim 2, wherein the PDGF concentration is about 0.3 mg/ml.

5. The method of claim 2, wherein the PDGF comprises PDGF-BB.

6. The method of claim 2, wherein the PDGF comprises recombinant human PDGF-BB (rhPDGF-BB).

7. The method of claim 6, wherein the rhPDGF-BB comprises at least 65% intact rhPDGF-BB.

8. The method of claim 2, wherein the calcium phosphate consists of particles having an average diameter from about 100 microns to about 300 microns.

9. The method of claim 2, wherein the calcium phosphate consists of particles having an average diameter from about 1000 microns to about 2000 microns.

10. The method of claim 2, wherein the calcium phosphate comprises a porosity greater than about 50%.

11. The method of claim 2, wherein the calcium phosphate comprises a porosity greater than about 90%.

12. The method of claim 2, wherein the calcium phosphate comprises β-tricalcium phosphate (β-TCP).

13. The method of claim 2, wherein the calcium phosphate comprises macroporosity.

14. The method of claim 2, wherein the calcium phosphate comprises a porosity that facilitates osteoinduction and osteoconduction into the biocompatible matrix.

15. The method of claim 2, wherein the bone scaffolding material consists of particles having an average diameter from about 100 to about 300 microns, wherein the PDGF concentration is about 0.1 to about 1.0 mg/ml, wherein the PDGF comprises rhPDGF-BB, and wherein the calcium phosphate consists of β-tricalcium phosphate.

16. The method of claim 15, wherein the calcium phosphate comprises a porosity greater than about 50%.

17. The method of claim 15, wherein the PDGF concentration is about 0.3 mg/ml.

18. The method of claim 2, wherein the bone scaffolding material consists of particles having an average diameter from about 1000 to about 2000 microns, wherein the PDGF concentration is about 0.1 to about 1.0 mg/ml, wherein the PDGF comprises rhPDGF-BB, and wherein the calcium phosphate consists of β-tricalcium phosphate.

19. The method of claim 18, wherein the calcium phosphate comprises a porosity greater than about 50%.

20. The method of claim 18, wherein the PDGF concentration is about 0.3 mg/ml.

21. The method of claim 2, wherein the bone scaffolding material consists of particles having an average diameter from about 250 to about 1000 microns, wherein the PDGF concentration is about 0.1 to about 1.0 mg/ml, wherein the PDGF comprises rhPDGF-BB, and wherein the calcium phosphate consists of β-tricalcium phosphate.

22. The method of claim 2, wherein the arthrodetic procedure further comprises the additional steps of aligning the bones to be fused and inserting at least one screw into at least one bone of the joint.

23. The method of claim 2, wherein the site of the desired bone fusion is selected from the group consisting of a subtalar joint, a talonavicular joint, a calcaneocuboid joint, and an ankle joint.

24. The method of claim 2, wherein the site of the desired bone fusion is a spinal joint.

25. The method of claim 1, wherein the biocompatible matrix consists of the bone scaffolding material and collagen.

26. The method of claim 25, wherein the PDGF concentration is about 0.1 to about 1.0 mg/ml.

27. The method of claim 25, wherein the PDGF concentration is about 0.3 mg/ml.

28. The method of claim 25, wherein the PDGF comprises PDGF-BB.

29. The method of claim 25, wherein the PDGF comprises recombinant human PDGF-BB (rhPDGF-BB).

30. The method of claim 29, wherein the rhPDGF-BB comprises at least 65% intact rhPDGF-BB.

31. The method of claim 25, wherein the calcium phosphate consists of particles having an average diameter from about 100 microns to about 300 microns.

32. The method of claim 25, wherein the calcium phosphate consists of particles having an average diameter from about 1000 microns to about 2000 microns.

33. The method of claim 25, wherein the calcium phosphate comprises a porosity greater than about 50%.

34. The method of claim 25, wherein the calcium phosphate comprises a porosity greater than about 90%.

35. The method of claim 25, wherein the calcium phosphate comprises β-tricalcium phosphate (β-TCP).

36. The method of claim 25, wherein the calcium phosphate comprises macroporosity.

37. The method of claim 25, wherein the calcium phosphate comprises a porosity that facilitates osteoinduction and osteoconduction into the biocompatible matrix.

38. The method of claim 25, wherein the bone scaffolding material consists of particles having an average diameter from about 100 to about 300 microns, wherein the PDGF concentration is about 0.1 to about 1.0 mg/ml, wherein the PDGF comprises rhPDGF-BB, and wherein the calcium phosphate consists of β-tricalcium phosphate.

39. The method of claim 38, wherein the calcium phosphate comprises a porosity greater than about 50%.

40. The method of claim 38, wherein the PDGF concentration is about 0.3 mg/ml.

41. The method of claim 25, wherein the bone scaffolding material consists of particles having an average diameter from about 1000 to about 2000 microns, wherein the PDGF concentration is about 0.1 to about 1.0 mg/ml, wherein the PDGF comprises rhPDGF-BB, and wherein the calcium phosphate consists of β-tricalcium phosphate.

42. The method of claim 41, wherein the calcium phosphate comprises a porosity greater than about 50%.

43. The method of claim 41, wherein the PDGF concentration is about 0.3 mg/ml.

44. The method of claim 25, wherein the bone scaffolding material consists of particles having an average diameter from about 250 to about 1000 microns, wherein the PDGF concentration is about 0.1 to about 1.0 mg/ml, wherein the PDGF comprises rhPDGF-BB, and wherein the calcium phosphate consists of β-tricalcium phosphate.

45. The method of claim 25, wherein the arthrodetic procedure further comprises the additional steps of aligning the bones to be fused and inserting at least one screw into at least one bone of the joint.

46. The method of claim 25, wherein the site of the desired bone fusion is selected from the group consisting of a subtalar joint, a talonavicular joint, a calcaneocuboid joint, and an ankle joint.

47. The method of claim 25, wherein the site of the desired bone fusion is a spinal joint.

48. The method of claim 25, wherein the collagen comprises Type I collagen.

49. The method of claim 25, wherein the composition is flowable.

50. The method of claim 25, where the ratio of collagen:calcium phosphate is about 20:80 by weight.

* * * * *